(12) United States Patent
Herrmann et al.

(10) Patent No.: US 11,730,789 B2
(45) Date of Patent: Aug. 22, 2023

(54) CELL PENETRATING ANTIBODIES

(71) Applicant: CITY OF HOPE, Duarte, CA (US)

(72) Inventors: Andreas Herrmann, Pasadena, CA (US); Hua Yu, Glendora, CA (US)

(73) Assignee: City of Hope, Duarte, CA (US)

( * ) Notice: Subject to any disclaimer, the term of this patent is extended or adjusted under 35 U.S.C. 154(b) by 280 days.

(21) Appl. No.: 15/543,915

(22) PCT Filed: Jan. 15, 2016

(86) PCT No.: PCT/US2016/013668
§ 371 (c)(1),
(2) Date: Jul. 14, 2017

(87) PCT Pub. No.: WO2016/115500
PCT Pub. Date: Jul. 21, 2016

(65) Prior Publication Data
US 2018/0008667 A1    Jan. 11, 2018

Related U.S. Application Data

(60) Provisional application No. 62/104,653, filed on Jan. 16, 2015.

(51) Int. Cl.
| | | |
|---|---|---|
| *A61K 38/14* | (2006.01) | |
| *C07K 16/18* | (2006.01) | |
| *A61K 47/54* | (2017.01) | |
| *C07K 16/00* | (2006.01) | |
| *A61P 35/00* | (2006.01) | |
| *A61K 39/08* | (2006.01) | |
| *A61K 38/00* | (2006.01) | |

(52) U.S. Cl.
CPC .............. *A61K 38/14* (2013.01); *A61K 39/08* (2013.01); *A61K 47/549* (2017.08); *A61P 35/00* (2018.01); *C07K 16/00* (2013.01); *C07K 16/18* (2013.01); *A61K 38/00* (2013.01); *C07K 2317/74* (2013.01); *C07K 2317/77* (2013.01)

(58) Field of Classification Search
None
See application file for complete search history.

(56) References Cited

U.S. PATENT DOCUMENTS

| | | | |
|---|---|---|---|
| 4,676,980 A | 6/1987 | Segal et al. | |
| 4,946,778 A | 8/1990 | Ladner et al. | |
| 5,235,033 A | 8/1993 | Summerton et al. | |
| 6,214,974 B1 | 4/2001 | Rosenblum et al. | |
| 8,586,708 B2 | 11/2013 | Ting et al. | |
| 2002/0151512 A1 | 10/2002 | Peyman et al. | |
| 2009/0186802 A1 | 7/2009 | Alluis et al. | |
| 2010/0239504 A1 | 9/2010 | Liu et al. | |
| 2011/0218334 A1 | 9/2011 | Maier et al. | |
| 2011/0251258 A1 | 10/2011 | Samarsky et al. | |

FOREIGN PATENT DOCUMENTS

| | | | |
|---|---|---|---|
| EP | 3038639 | * | 7/2016 |
| WO | WO-2015/031837 A1 | | 3/2015 |
| WO | WO-2017/004357 A1 | | 1/2017 |
| WO | WO-2017/024239 A1 | | 2/2017 |

OTHER PUBLICATIONS

ThermoFisher Scientific (<https://www.thermofisher.com/us/en/home/life-science/protein-biology/protein-biology-learning-center/protein-biology-resource-library/pierce-protein-methods/avidin-biotin-interaction.html> available Jan. 2, 2011).*
Santa Cruz Biotechnology (CD71(OX26): sc-53059, accessed Aug. 29, 2019).*
Daniels et al. (Biochim Biophys Acta. 2012; 1820(3):291-317).*
Costantini et al. (111In-labeled Trastuzumab (Herceptin) modified with nuclear localization sequence (NLs): an Auger electron emitting radiotherapeutic agent for HER2/neu amplified breast cancer; J. Nucl Med 2007;48:1357-1368).*
Drugbank (https://go.drugbank.com/drugs/DB00072 Jun. 13, 2005).*
Arnon, R. et al. (1985). "Monoclonal Antibodies for Immunotargeting of Drugs in Cancer Therapy," in Monoclonal Antibodies and Cancer Therapy Reisfeld et al. (eds.), pp. 243-256 (Alan R. Liss, Inc. 1985).
Boado, R.J. et al. (Nov. 1, 1998). "Drug Delivery of Antisense Molecules to the Brain for Treatment of Alzheimer's Disease and Cerebral Aids," *Journal of Pharmaceutical Sciences* 87(11):1308-1315.
Chonn, A. et al. (Dec. 1995). "Recent advances in liposomal drug-delivery systems," *Curr Opin Biotechnol* 6(6):698-708.
Dickson, C. et al. (2008). "Protein techniques: immunoprecipitation, in vitro kinase assays, and Western blotting," *Methods Mol Biol* 461:735-744.
Extended European Search Report dated Jul. 6, 2018, for EP Patent Application No. 16737990.8, 10 pages.
International Search Report dated Apr. 1, 2016, for PCT Application No. PCT/US2016/013668, filed Jan. 15, 2016, 3 pages.
Written Opinion dated Apr. 1, 2016, for PCT Application No. PCT/US2016/013668, filed Jan. 15, 2016, 7 pages.

* cited by examiner

*Primary Examiner* — Julie Ha
*Assistant Examiner* — Tara L Martinez
(74) *Attorney, Agent, or Firm* — Mintz Levin Cohn Ferris Glovsky and Popeo, P.C.

(57) ABSTRACT

Provided herein are cell penetrating conjugates. The conjugates include a non-cell penetrating protein attached to a phosphorothioate nucleic acid or phosphorothioate polymer backbone through a non-covalent linker including a biotin-binding domain and a biotin domain, wherein the phosphorothioate nucleic acid or phosphorothioate polymer backbone enhances intracellular delivery of the non-cell penetrating protein. Also provided are compositions and kits comprising the conjugates.

13 Claims, 18 Drawing Sheets

CELL PENETRATING ANTIBODIES

CROSS-REFERENCES TO RELATED APPLICATIONS

This application is a National Stage filing of International Patent Application No. PCT/US2016/013668, filed on Jan. 15, 2016, which claims benefit of U.S. Provisional Patent Application No. 62/104,653, filed on Jan. 16, 2015, the contents of which are hereby incorporated by reference in their entireties for all purposes.

STATEMENT AS TO RIGHTS TO INVENTIONS MADE UNDER FEDERALLY SPONSORED RESEARCH AND DEVELOPMENT

This invention was made using support under Grant Number CA122976 awarded by the National Institutes of Health. The government has certain rights to this invention.

BACKGROUND OF THE INVENTION

Antibodies have proven to be an efficacious drug modality for its easy generation, specificity and bio-durability relative to other types of drugs such as small molecule drugs. Current antibody therapy can only target extracellular molecules. However, numerous important targets for disease treatment and disease diagnosis are intracellular. For example, a number of transcriptional factors, such as STAT3, are among the most crucial yet challenging targets for cancer therapy. Provided herein are solutions for these and other needs in the art.

BRIEF SUMMARY OF THE INVENTION

In one aspect, a cell-penetrating conjugate is provided. The cell-penetrating conjugate includes (i) a non-cell penetrating protein, (ii) a phosphorothioate nucleic acid and (iii) a non-covalent linker attaching the phosphorothioate nucleic acid to the non-cell penetrating protein. The non-covalent linker includes a biotin-binding domain non-covalently attached to a biotin domain and the phosphorothioate nucleic acid enhances intracellular delivery of the non-cell penetrating protein.

In another aspect, a method of forming a cell penetrating conjugate is provided. The method includes contacting a non-cell penetrating protein with a phosphorothioate nucleic acid, wherein the non-cell penetrating protein is attached to a first member of a biotin binding pair and the phosphorothioate nucleic acid is attached to a second member of the biotin binding pair, thereby forming a cell penetrating conjugate, which includes a non-covalent bond between a biotin domain and biotin-binding domain.

In another aspect, a cell including the cell penetrating conjugate provided herein including embodiments thereof is provided.

In another aspect, a pharmaceutical composition including the cell penetrating conjugate provided herein including embodiments thereof and a pharmaceutically acceptable carrier is provided.

In another aspect, a kit including the cell penetrating conjugate provided herein including embodiments thereof or the pharmaceutical composition as provided herein including embodiments thereof and instructions for use are provided.

In another aspect, a method of delivering a non-cell penetrating protein into a cell is provided. The method includes contacting the cell with the cell penetrating conjugate as provided herein including embodiments thereof.

In another aspect, a method of treating a disease in a subject in need thereof is provided. The method includes administering to a subject an effective amount of the cell penetrating conjugate as provided herein including embodiments thereof, thereby threating the disease in the subject.

BRIEF DESCRIPTION OF THE DRAWINGS

FIG. 4A, Single cell suspensions were prepared and rabbit IgG was assessed by intracellular staining procedure analyzed by flow cytometry. FIG. 4B, Whole cell lysates were prepared and cleared from cell debris before agarose beads were added and incubated with lysates at 4° C. overnight shaking. Proteins were separated by SDS-PAGE, transferred onto nitrocellulose membrane, and probed for STAT3 protein. —PEG, Polyethylene glycol.

DETAILED DESCRIPTION OF THE INVENTION

Definitions

Figure 1:
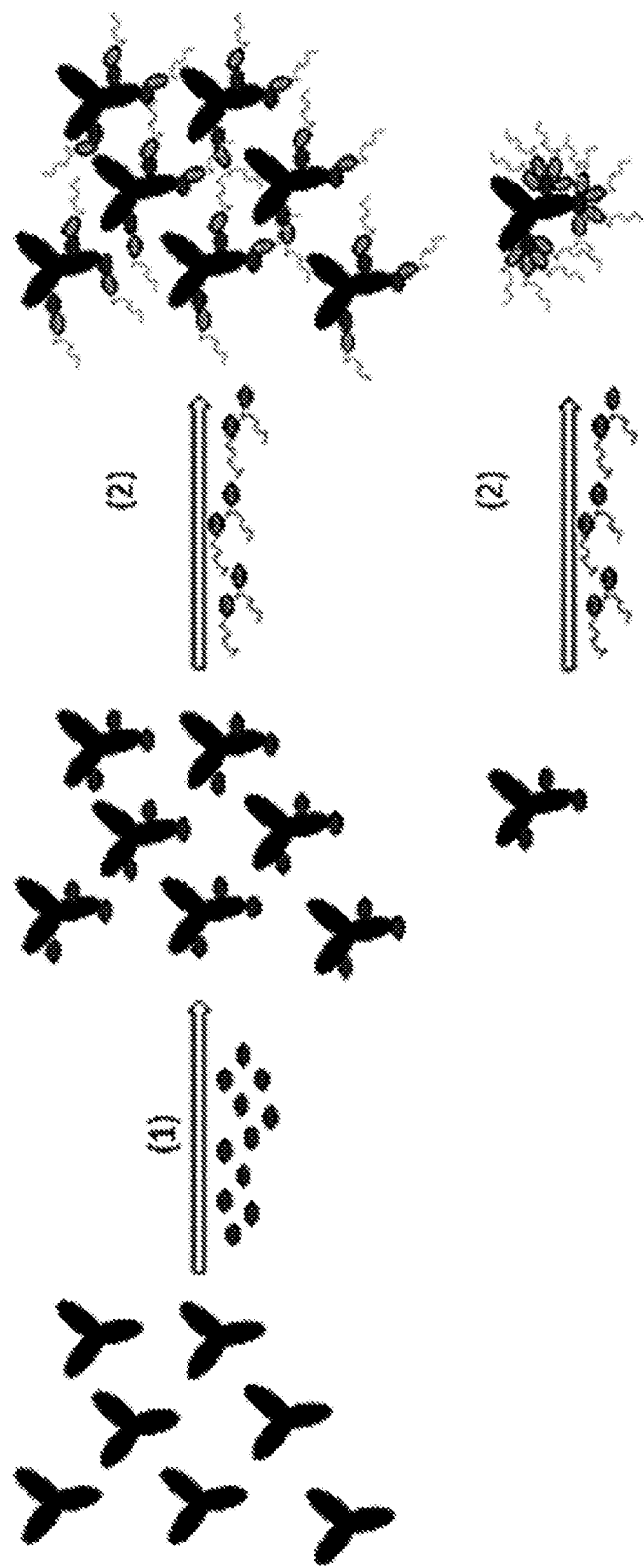
FIG. 1: Conjugation scheme: Avidin to antibody/peptide and biotin-oligo to avidin. (1) Avidinylation of IgG; (2) add biotinylated delivery entity (i.e. PS-oligomers). Instead of avidin, streptavidin (or avidin derivatives) may be used; streptavidin provides the opportunity to accept 4 biotins, while avidin accepts just 1 biotin. PS, phosphothioate
Figure 2:
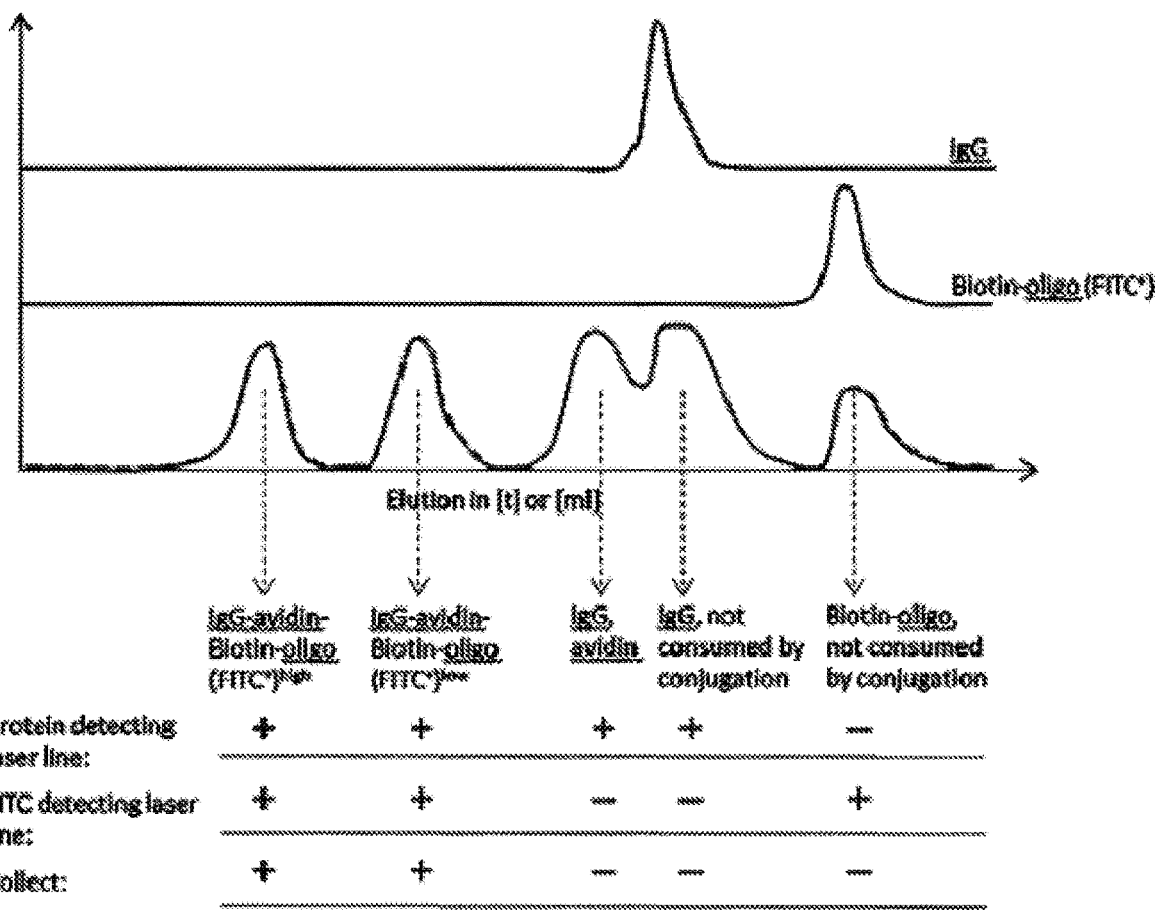
FIG. 2: Purification scheme: Avidin/Biotin driven conjugation increases molecular weight enabling purification of modified antibodies
Figure 3:
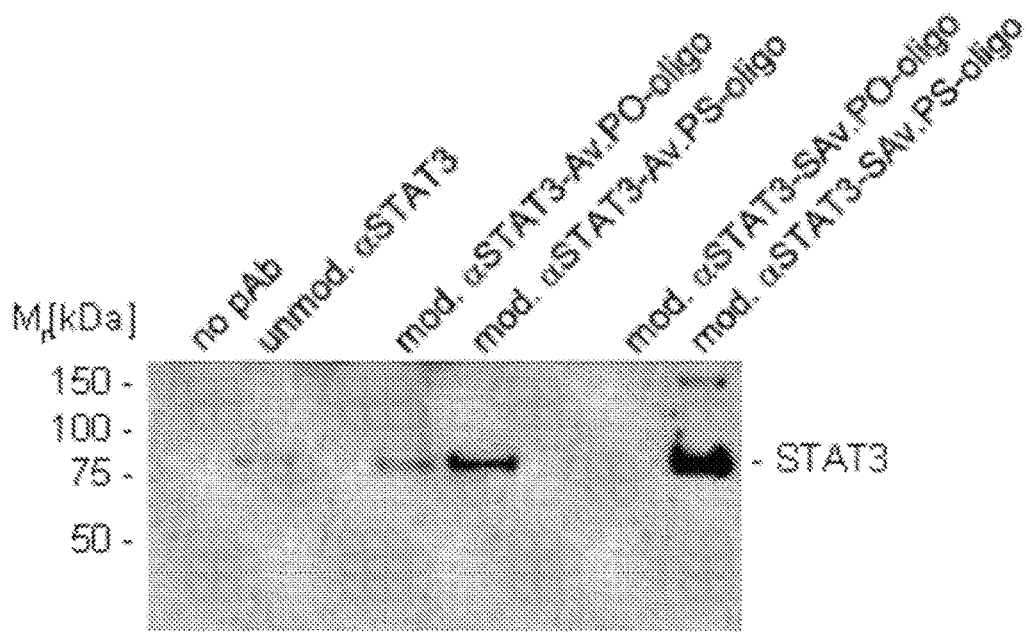
FIG. 3: Non-covalent linkage of DNA-oligo's via avidin-biotin to antibody protein enables antibody/protein cell-penetrating/antigen recognition. Human glioma U251 cells were incubated with anti-STAT3 antibodies modified as indicated for 1 h at 10 mg/ml. Whole cell lysates were prepared and cleared from cell debris before agarose beads were added and incubated with lysates at 4° C. overnight with shaking. Proteins were separated by SDS-PAGE, transferred onto nitrocellulose membrane, and probed for STAT3 protein with antibody. Av, Avidin; SAv, Streptavidin; B, Biotin; PO, phosphate; PS, phosphothioate

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" or "oligonucleotide" or "polynucleotide" or grammatical equivalents used herein means at least two nucleotides covalently linked together. The term "Nucleic acid" refers to deoxyribonucleotides or ribonucleotides and polymers thereof in either single- or double-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, and 2-O-methyl ribonucleotides.

The term "phosphorothioate nucleic acid" refers to a nucleic acid in which one or more internucleotide linkages are through a phosphorothioate moiety (thiophosphate) moiety. The phosphorothioate moiety may be a monothiophosphate ($-P(O)_3(S)^{3-}-$) or a dithiophosphate ($-P(O)_2(S)_2^{3-}-$). In embodiments, the phosphorothioate moiety is a monothiophosphate ($-P(O)_3(S)^{3-}-$). In embodiments, the phosphorothioate nucleic acid is a monothiophosphate nucleic acid. In embodiments, one or more of the nucleosides of a phosphorothioate nucleic acid are linked through a phosphorothioate moiety (e.g. monothiophosphate) moiety, and the remaining nucleosides are linked through a phosphodiester moiety ($-P(O)_4^{3-}-$). In embodiments, one or more of the nucleosides of a phosphorothioate nucleic acid are linked through a phosphorothioate moiety (e.g. monothiophosphate) moiety, and the remaining nucleosides are linked through a methylphosphonate linkage. In embodiments, all the nucleosides of a phosphorothioate nucleic acid are linked through a phosphorothioate moiety (e.g. a monothiophosphate) moiety.

Phosphorothioate oligonucleotides (phosphorothioate nucleic acids) are typically from about 5, 6, 7, 8, 9, 10, 12, 15, 20, 25, 30, 40, 50 or more nucleotides in length, up to about 100 nucleotides in length. Phosphorothioate nucleic acids may also be longer in lengths, e.g., 200, 300, 500, 1000, 2000, 3000, 5000, 7000, 10,000, etc. As described above, in certain embodiments. the phosphorothioate nucleic acids herein contain one or more phosphodiester bonds. In other embodiments, the phosphorothioate nucleic acids include alternate backbones (e.g., mimics or analogs of phosphodiesters as known in the art, such as, boranophosphate, methylphosphonate, phosphoramidate, or O-methylphosphoroamidite linkages (see Eckstein, Oligonucleotides and Analogues: A Practical Approach, Oxford University Press). The phosphorothioate nucleic acids may also include one or more nucleic acid analog monomers known in the art, such as, peptide nucleic acid monomer or polymer, locked nucleic acid monomer or polymer, morpholino monomer or polymer, glycol nucleic acid monomer or polymer, or threose nucleic acid monomer or polymer.

Other analog nucleic acids include those with positive backbones; non-ionic backbones, and nonribose backbones, including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. Phosphorothioate nucleic acids and phosphorothioate polymer backbones can be linear or branched. For example, the branched nucleic acids are repetitively branched to form higher ordered structures such as dendrimers and the like.

As used herein, a "phosphorothioate polymer backbone" is a chemical polymer with at least two phosphorothioate linkages (e.g. monothiophosphate) (e.g. linking together sugar subunits, cyclic subunits or alkyl subunits). The phosphorothioate polymer backbone may be a phosphorothioate sugar polymer, which is a phosphorothioate nucleic acid in which one or more (or all) of the chain of pentose sugars lack the bases (nucleobases) normally present in a nucleic acid. The phosphorothioate polymer backbone can include two or more phosphorothioate linkages. The phosphorothioate polymer backbone can include 5, 6, 7, 8, 9, 10, 12, 15, 25, 30, 40, 50 or more linkages and can contain up to about 100 phosphorothioate linkages. Phosphorothioate polymer backbones may also contain a larger number of linkages, e.g., 200, 300, 500, 1000, 2000, 3000, 5000, 7000, 10,000, and the like.

The phosphorothioate nucleic acids and phophorothioate polymer backbones may be partially or completely phosphorothioated. For example, 50% or more of the interneucleotide linkages of a phosphorothioate nucleic acid can be phosphorothioate linkages. In embodiments, 5%, 10%, 15%, 20%, 25%, 30%, 35%, 40%, 45%, 50%, 55%, 60%, 65%, 70%, 75%, 80%, 85%, 90%, 95%, or 99% of the internucleotide linkages of a phosphorothioate nucleic acid are phosphorothioate linkages. In embodiments, 50%, 55%, 60%, 65%, 70%, 75%, 80%, 85%, 90%, 95%, or 99% of the internucleotide linkages of a phosphorothioate nucleic acid are phosphorothioate linkages. In embodiments, 75%, 80%, 85%, 90%, 95%, or 99% of the internucleotide linkages of a phosphorothioate nucleic acid are phosphorothioate linkages. In embodiments, 90%, 95%, or 99% of the internucleotide linkages of a phosphorothioate nucleic acid are phosphorothioate linkages. In embodiments, the remaining internucleotide linkages are phosphodiester linkages. In embodiments, the remaining internucleotide linkages are methylphosphonate linkages. In embodiments, 100% of the internucleotide linkages of the phosphorothioate nucleic acids are phosphorothioate linkages. Similarly, 5%, 10%, 15%, 20%, 25%, 30%, 35%, 40%, 45%, 50%, 55%, 60%, 65%, 70%, 75%, 80%, 85%, 90%, 95%, or 99%, of the intersugar linkages in a phosphorothioate polymer backbone can be phosphorothioate linkages. In embodiments, 50%, 55%, 60%, 65%, 70%, 75%, 80%, 85%, 90%, 95%, or 99%, of the intersugar linkages in a phosphorothioate polymer backbone can be phosphorothioate linkages. In embodiments, 75%, 80%, 85%, 90%, 95%, or 99%, of the intersugar linkages in a phosphorothioate polymer backbone can be phosphorothioate linkages. In embodiments, 90%, 95%, or 99%, of the intersugar linkages in a phosphorothioate polymer backbone can be phosphorothioate linkages. In embodiments, the remaining internucleotide linkages are phosphodiester linkages. In embodiments, the remaining internucleotide linkages are methylphosphonate linkages. In embodiments, 100% of the intersugar linkages of the phosphorothioate polymer backbone are phosphorothioate linkages.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism. An "inhibitory nucleic acid" is a nucleic acid (e.g. DNA, RNA, polymer of nucleotide analogs) that is capable of binding to a target nucleic acid (e.g. an mRNA translatable into a protein) and reducing transcription of the target nucleic acid (e.g. mRNA from DNA) or reducing the translation of the target nucleic acid (e.g. mRNA) or altering transcript splicing (e.g. single stranded morpholino oligo).

A "labeled nucleic acid or oligonucleotide" is one that is bound, either covalently, through a linker or a chemical bond, or noncovalently, through ionic, van der Waals, electrostatic, or hydrogen bonds to a label such that the presence of the nucleic acid may be detected by detecting the presence of the detectable label bound to the nucleic acid. Alternatively, a method using high affinity interactions may achieve the same results where one of a pair of binding partners binds to the other, e.g., biotin, streptavidin. In embodiments, the phosphorothioate nucleic acid or phosphorothioate polymer backbone includes a detectable label, as disclosed herein and generally known in the art.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual,* 18.1-18.88.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. Transgenic cells and plants are those that express a heterologous gene or coding sequence, typically as a result of recombinant methods.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion The term "exogenous" refers to a molecule or substance (e.g., a compound, nucleic acid or protein) that originates from outside a given cell or organism. For example, an "exogenous promoter" as referred to herein is a promoter that does not originate from the plant it is expressed by. Conversely, the term "endogenous" or "endogenous promoter" refers to a molecule or substance that is native to, or originates within, a given cell or organism.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

The term "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. In some embodiments, antibodies or fragments of antibodies may be derived from different organisms, including humans, mice, rats, hamsters, camels, etc. Antibodies of the invention may include antibodies that have been modified or mutated at one or more amino acid positions to improve or modulate a desired function of the antibody (e.g. glycosylation, expression, antigen recognition, effector functions, antigen binding, specificity, etc.).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. The Fc (i.e. fragment crystallizable region) is the "base" or "tail" of an immunoglobulin and is typically composed of two heavy chains that contribute two or three constant domains depending on the class of the antibody. By binding to specific proteins the Fc region ensures that each antibody generates an appropriate immune response for a given antigen. The Fc region also binds to various cell receptors, such as Fc receptors, and other immune molecules, such as complement proteins.

Antibodies exist, for example, as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially the antigen dinging portion with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa.

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633, 425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

Techniques for conjugating therapeutic agents to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery ($2^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)). As used herein, the term "antibody-drug conjugate" or "ADC" refers to a therapeutic agent conjugated or otherwise covalently bound to an antibody. A "therapeutic agent" as referred to herein, is a composition useful in treating or preventing a disease such as cancer.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

A "ligand" refers to an agent, e.g., a polypeptide or other molecule, capable of binding to a receptor.

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

The term "biotin" as provided herein refers to compound characterized by a ureido (tetrahydroimidizalone) ring fused with a tetrahydrothiophene ring. "Biotin" as provided herein refers to 5-[(3aS,4S,6aR)-2-oxohexahydro-1H-thieno[3,4-d] imidazol-4-yl]pentanoic acid, and in the customary sense, refers to CAS Registry No. 58-85-5. A "biotin-binding domain" as used herein is a protein domain that is capable of binding a biotin. Non-limiting examples of biotin-binding domains include avidin, streptavidin and neutravidin.

The term "avidin" or "streptavidin" as provided herein includes any of the avidin or streptavidin naturally occurring forms, homologs, variants or derivatives (e.g., neutravidin) that maintain the activity of the naturally occurring form (e.g., within at least 50%, 80%, 90%, 95%, 96%, 97%, 98%, 99% or 100% activity compared to the native protein). In some embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a biotin domain as described herein and a biotin-binding domain. In embodiments contacting includes, for example, allowing a biotin domain as described herein to interact with a biotin-binding domain.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

The terms "disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma). The disease may be an autoimmune, inflammatory, cancer, infectious, metabolic, developmental, cardiovascular, liver, intestinal, endocrine, neurological, or other disease.

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

As used herein, an "autoimmune disease" refers to a disease or disorder that arises from altered immune reactions by the immune system of a subject, e.g., against substances tissues and/or cells normally present in the body of the subject. Autoimmune diseases include, but are not limited to, arthritis, rheumatoid arthritis, psoriatic arthritis, juvenile idiopathic arthritis, scleroderma, systemic scleroderma, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, Behcet's disease, Crohn's disease, ulcerative colitis, bullous pemphigoid, sarcoidosis, psoriasis, ichthyosis, Graves ophthalmopathy, inflammatory bowel disease, Addison's disease, Vitiligo, asthma, and allergic asthma.

As used herein, an "inflammatory disease" refers to a disease or disorder associated with abnormal or altered inflammation. Inflammation is a biological response initiated by the immune system as part of the healing process in response to a pathogen, damaged cells or tissues or irratants.

Chronic inflammation can lead to a variety of diseases. Inflammatory diseases include, but are not limited to, atherosclerosis, allergies, asthma, rheumatoid arthritis, transplant rejection, celiac disease, chronic prostatitis, inflammatory bowel diseases, pelvic inflammatory diseases, and inflammatory myopathies.

As used herein, "metabolic disorders" refer to diseases or disorders involving abnormal metabolism of a variety of molecules and substances including, for example, carobydrates, amino acids, organic acids. Metabolic disorders include, but are not limited to, disorders of carbohydrate metabolism, e.g., glycogen storage disease, disorders of amino acid metabolism, e.g., phenylketonuria, maple syrup urine disease, glutaric acidemia type 1, urea cycle disorder or urea cycle defects, e.g., carbamoyl phosphate synthetase I deficiency, disorders of organic acid metabolism (organic acidurias), e.g., alcaptonuria, disorders of fatty acid oxidation and mitochondrial metabolism, e.g., medium-chain acyl-coenzyme A dehydrogenase deficiency, disorders of porphyrin metabolism, e.g., acute intermittent porphyria, disorders of purine or pyrimidine metabolism, e.g., Lesch-Nyhan syndrome, disorders of steroid metabolism, e.g., lipoid congenital adrenal hyperplasia, congenital adrenal hyperplasia, disorders of mitochondrial function, e.g., Kearns-Sayre syndrome, disorders of peroxisomal function, e.g., Zellweger syndrome, and lysosomal storage disorders, e.g., Gaucher's disease, and Niemann Pick disease.

As used herein, "developmental disorders" refer to diseases or disorders often originating in childhood associated with language disorders, learning disorders, motor disorders and neurodevelopmental disorders. Examples include, but are not limited to, autism spectrum disorders and attention deficit disorders.

As used herein, "cardiovascular diseases" refer to diseases associated with the heart, blood vessels or both. Cardiovascular diseases include, but are not limited to, coronary heart disease, cardiomyopathy, hypertensive heart disease, heart failure, cardiac dysrhythmias, inflammatory heart disease, peripheral arterial disease, cerebrovascular disease and inflammatory heart disease.

As used herein, "liver diseases" refer to diseases associated with the abnormalities in the liver and/or liver function. Liver diseases include, but are not limited to, hepatitis, alcoholic liver disease, fatty liver disease, cirrhosis, Budd-Chiari syndrome, Gilbert's syndrome and cancer.

As used herein, the term "intestinal disease" refers to diseases or disorders associated with abnormalities in the intestine (small or large). Intestinal diseases include, but are not limited to, gastroenteritis, colitis, ileitis, appendicitis, coeliac disease, Crohn's disease, enteroviruses, irritable bowel syndrome, and diverticular disease.

As used herein, the term "endocrine disease" refers to diseases or disorders of the endocrine system including endocrine gland hyposecretion, endocrine gland hypersecretion and tumors. Endocrine diseases include, but are not limited to, Addison's disease, diabetes, Conn's syndrome, Cushing's syndrome, glucocorticoid remediable aldosteronism, hypoglycemia, hyperthyroidism, hypothyroidism, thyroiditis, hypopituitarism, hypogonadism and parathyroid gland disorders.

As used herein, the term "neurological disorder" refers to diseases or disorders of the bodies nervous system including structural, biochemical or electrical abnormalities. Neurological disorders include, but are not limited to, brain damage, brain dysfunction, spinal cord disorders, peripheral neuropathies, cranial nerve disorders, autonomic nervous system disorders, seizure disorders, movement disorders, e.g., Parkinson's disease and Multiple Sclerosis, and central neuropathies.

As used herein, the term "infectious disease" refers to diseases or disorders associate with infection, presence and/or growth of a pathogenic agent in a host subject. Infectious pathogenic agents include, but are not limited to, viruses, bacteria, fungi, protozoa, multicellular parasites and aberrant proteins, e.g., prions. Viruses associated with infectious disease include but are not limited to, herpes simplex viruses, cytomegalovirus, Epstein-Barr virus, Varicella-zoster virus, herpesviruses, Vesicular stomatitis virus, Hepatitis viruses, Rhinovirus, Coronavirus, Influenza viruses, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Simian Immunodeficiency viruses, Human Immunodeficiency viruses. Bacteria associated with infectious disease include, but are not limited to, *M. tuberculosis, Salmonella* species, *E. coli, Chlamydia* species, *Staphylococcus* species, *Bacillus* species, and *Pseudomonas* species.

The term "associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) is caused by (in whole or in part), or a symptom of the disease is caused by (in whole or in part) the substance or substance activity or function.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by using a method as described herein), results in reduction of the disease or one or more disease symptoms.

As used herein, the terms "cell-penetrating" or "cell-penetration" refer to the ability of a molecule (e.g. a protein) to pass from the extracellular environment into a cell in a significant or effective amount. Thus, a cell-penetrating conjugate is a molecule that passes from the extracellular environment, through the membrane, and into a cell.

As used herein, the terms "non-cell penetrating" or "non-cell penetration" refers to the inability of a molecule to pass from the extracellular environment into a cell in a significant or effective amount. Thus, non-cell penetrating peptides or proteins generally are not capable of passing from the extracellular environment, through the cell membrane, and into a cell in order to achieve a significant biological effect on a population of cells, organ or organism. The term does not exclude the possibility that one or more of the small number of peptides or proteins may enter the cell. However, the term refers to molecules that are generally not able to enter a cell from the extracellular environment to a significant degree. Examples of non-cell penetrating molecules and substances include, but are not limited to, large molecules such as, for example, high molecular weight proteins. Peptides or proteins can be determined to be non-cell penetrating using methods known to those of skill in the art. By way of example, a peptide or protein can be fluorescently labeled and the ability of the peptide or protein to pass from the extracellular environment into the cell can be determined in vitro by flow cytometric analysis or confocal microscopy. In some embodiments, a "non-cell penetrating protein" refers to a protein that penetrates a cell at least about 2, 3, 4, 5, 6, 7, 8, 9, 10, 20, 30, 40, 50, 60, 70, 80, 90, 100, 200, 300, 400, 500, 600, 700, 800, 900, 1000, 10,000 or 100,000 fold less than the same protein attached to a phosphorothioate nucleic acid or phosphorothioate polymer backbone. In some embodiments, a "non-cell penetrating protein" refers to a protein that does not measurably penetrate a cell.

As used herein, "molecular weight" (M.W.) or "molecular mass" refers to the sum of the atomic weights of all the atoms in a molecule. With respect to molecules, a molecule with a high molecular weight typically has a molecular weight of 25 kDa or more. By way of example, a high molecular weight protein can have a M.W. from about 25 kDa to 1000 kDa or more.

As used herein, the term "intracellular" means inside a cell. As used herein, an "intracellular target" is a target, e.g., nucleic acid, polypeptide or other molecule (e.g., carbohydrate) that is located inside of a cell and is a target to which the non-cell penetrating proteins provided herein bind. Binding can be direct or indirect. In embodiments, the non-cell penetrating protein selectively binds the intracellular target. By selectively binds, selectively binding, or specifically binding refers to the agent (e.g., a non-cell penetrating protein) binding one agent (e.g., intracellular target) to the partial or complete exclusion of other agents. By binding is meant a detectable binding at least about 1.5 times the background of the assay method. For selective or specific binding such a detectable binding can be detected for a given agent but not a control agent. Alternatively, or additionally, the detection of binding can be determined by assaying the presence of down-stream molecules or events.

As used herein, the term "conjugate" refers to the association between atoms or molecules. The association can be direct or indirect. For example, a conjugate between a nucleic acid and a protein can be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the phosphorothioate nucleic acid, phosphorothioate backbone polymer or non-cell penetrating protein are non-covalently attached to the biotin-binding domain or biotin domain through a non-covalent chemical reaction between a component of the phosphorothioate nucleic acid, phosphorothioate backbone polymer (e.g. a monothiophosphate) or non-cell penetrating protein and a component of the biotin-binding domain or biotin domain (e.g. an amino acid). In other embodiments, the phosphorothioate nucleic acid, phosphorothioate backbone polymer or non-cell penetrating protein include one or more reactive moieties, e.g., a covalent reactive moiety, as described herein (e.g., an amino acid reactive moiety such as a vinyl sulfone moiety ($-S(O)_2CH=CH_2$).

Useful reactive moieties including covalent reactive moieties or functional groups used for conjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding;

(m) metal bonding to reactive phosphorus groups (e.g. phosphines) to form, for example, phosphate diester bonds; and (n) sulfones, for example, vinyl sulfone.

The reactive functional groups can be chosen such that they do not participate in, or interfere with, the chemical stability of the proteins described herein. By way of example, the nucleic acids can include a vinyl sulfone or other reactive moiety. For example, a nucleic acid with a vinyl sulfone reactive moiety may be formed from a nucleic acid with an S—S—R moiety, wherein R is $-(CH_2)_6-OH$. A nucleic acid with a vinyl sulfone may further be formed from a nucleic acid with a terminal phosphate (PS).

A "control" or "standard control" refers to a sample, measurement, or value that serves as a reference, usually a known reference, for comparison to a test sample, measurement, or value. For example, a test sample can be taken from a patient suspected of having a given disease (e.g. an autoimmune disease, inflammatory autoimmune disease, cancer, infectious disease, immune disease, or other disease) and compared to a known normal (non-diseased) individual (e.g. a standard control subject). A standard control can also represent an average measurement or value gathered from a population of similar individuals (e.g. standard control subjects) that do not have a given disease (i.e. standard control population), e.g., healthy individuals with a similar medical background, same age, weight, etc. A standard control value can also be obtained from the same individual, e.g. from an earlier-obtained sample from the patient prior to disease onset. One of skill will recognize that standard controls can be designed for assessment of any number of parameters (e.g. RNA levels, protein levels, specific cell types, specific bodily fluids, specific tissues, synoviocytes, synovial fluid, synovial tissue, fibroblast-like synoviocytes, macrophage like synoviocytes, etc).

One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

The term "diagnosis" refers to a relative probability that a disease (e.g. an autoimmune, inflammatory autoimmune, cancer, infectious, immune, or other disease) is present in the subject. Similarly, the term "prognosis" refers to a relative probability that a certain future outcome may occur in the subject with respect to a disease state. For example, in the context of the present invention, prognosis can refer to the likelihood that an individual will develop a disease (e.g. an autoimmune, inflammatory autoimmune, cancer, infectious, immune, or other disease), or the likely severity of the disease (e.g., duration of disease). The terms are not intended to be absolute, as will be appreciated by any one of skill in the field of medical diagnostics.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "cell" as used herein, refers to a cell carrying out metabolic or other functions sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

Cell-Penetrating Conjugates

Provided herein are, inter alia, cell-penetrating conjugates including a non-cell penetrating protein (e.g., antibody) attached to a phosphorothioate nucleic acid or a phosphorothioate polymer backbone. The non-cell penetrating protein is attached to the phosphorothioate nucleic acid or the phosphorothioate polymer backbone through a non-covalent linker, which includes a first member of a biotin binding pair and a second member of a biotin binding pair. The first member of the biotin binding pair may be a biotin-binding domain (e.g., avidin, streptavidin) or a biotin domain (e.g., biotin). The second member of the biotin binding pair may be a biotin-binding domain (e.g., avidin, streptavidin) or a biotin domain (e.g., biotin). The non-covalent linker is formed through non-covalent binding between the first member of the biotin binding pair and the second member of the biotin binding pair. In embodiments, the first member of the biotin binding pair is a biotin-binding domain (e.g., avidin, streptavidin) and the second member of the biotin binding pair is a biotin domain (e.g., biotin). In embodiments, the first member of the biotin binding pair is a biotin domain (e.g., biotin) and the second member of the biotin binding pair is a biotin-binding domain (e.g., avidin, streptavidin).

The first member of the biotin binding pair and the second member of the biotin binding pair may be covalently or non-covalently attached to the non-cell penetrating protein, the phosphorothioate nucleic acid or phosphorothioate polymer backbone. In embodiments, the non-cell penetrating protein is covalently attached to the first member of the biotin binding pair (e.g., avidin, streptavidin) and the phosphorothioate nucleic acid or the phosphorothioate polymer backbone is covalently attached to the second member of the biotin binding pair (e.g., biotin). Attachment of the phosphorothioate nucleic acid or the phosphorothioate polymer backbone through the non-covalent linker forms the non-cell penetrating protein provided herein capable of to enter a cell through penetration. The conjugates provided herein are useful, inter alia, for the intracellular delivery of antibodies and targeting of intracellular targets (e.g., signaling proteins) for therapeutic and diagnostic purposes.

In one aspect, a cell-penetrating conjugate is provided. The cell-penetrating conjugate includes (i) a non-cell penetrating protein, (ii) a phosphorothioate nucleic acid and (iii) a non-covalent linker attaching the phosphorothioate nucleic acid to the non-cell penetrating protein. The non-covalent linker includes a biotin-binding domain non-covalently attached to a biotin domain and the phosphorothioate nucleic acid enhances intracellular delivery of the non-cell penetrating protein.

The non-cell penetrating protein may be attached to a phosphorothioate polymer backbone through a non-covalent linker. Thus, in another aspect, a cell-penetrating conjugate is provided. The cell-penetrating conjugate includes (i) a non-cell penetrating protein, (ii) a phosphorothioate polymer backbone and (iii) a non-covalent linker attaching the phosphorothioate polymer backbone to the non-cell penetrating protein. The non-covalent linker includes a biotin-binding domain non-covalently attached to a biotin domain and the phosphorothioate polymer backbone enhances intracellular delivery of the non-cell penetrating protein. As discussed above, polymer backbones contain the same structure (i.e., contains a chain of two or more sugar residues linked together) as a nucleic acid sequence with the exception that the polymer backbone lacks the bases normally present in a nucleic acid sequence. Also provided are cells comprising the cell penetrating conjugates.

In embodiments, the biotin-binding domain is an avidin domain. In embodiments, the biotin-binding domain is a streptavidin domain. In embodiments, the streptavidin domain binds a plurality of biotin domains. In embodiments, the streptavidin domain binds about four biotin domains. In embodiments, the biotin-binding domain is attached to the non-cell penetrating protein. In embodiments, the biotin-binding domain is covalently attached to the non-cell penetrating protein. In embodiments, the biotin-binding domain is non-covalently attached to the non-cell penetrating protein. In embodiments, a plurality of biotin-binding domains are attached to the non-cell penetrating protein. In embodiments, the biotin-binding domain is attached to the phosphorothioate nucleic acid or phosphorothioate polymer backbone. In embodiments, the biotin-binding domain is covalently attached to the phosphorothioate nucleic acid or phosphorothioate polymer backbone. In embodiments, the biotin-binding domain is non-covalently attached to the phosphorothioate nucleic acid or phosphorothioate polymer backbone. In embodiments, a plurality of biotin-binding domains are attached to the phosphorothioate nucleic acid or phosphorothioate polymer backbone. In embodiments, the biotin-binding domain is non-covalently attached to the biotin domain, thereby forming the non-covalent linker.

In embodiments, the biotin domain is attached to the phosphorothioate nucleic acid or the phosphorothioate polymer backbone. In embodiments, the biotin domain is covalently attached to the phosphorothioate nucleic acid or the phosphorothioate polymer backbone. In embodiments, the biotin domain is non-covalently attached to the phosphorothioate nucleic acid or the phosphorothioate polymer backbone. In embodiments, a plurality of phosphorothioate nucleic acids or phosphorothioate polymer backbones are attached to the biotin domain. In embodiments, the biotin domain is attached to the non-cell penetrating protein. In embodiments, the biotin domain is covalently attached to the non-cell penetrating protein. In embodiments, the biotin domain is non-covalently attached to the non-cell penetrating protein. In embodiments, a plurality of biotin domains are attached to non-cell penetrating protein. In embodiments, the biotin domain is non-covalently attached to the biotin-binding domain, thereby forming the non-covalent linker.

As discussed above, the nucleic acids, e.g., the phosphorothioate nucleic acids or phosphorothiate polymer backbones are attached to the non-cell penetrating proteins through a non-covalent linker including a biotin-binding domain (e.g., avidin or streptavidin) and a biotin domain. The nucleic acids, e.g., the phosphorothioate nucleic acids or phosphorothiate polymer backbones may be attached to the biotin-binding domain or the biotin domain through a variety of mechanisms. Similarly, the non-cell penetrating proteins may be attached to the biotin-binding domain or the biotin domain through a variety of mechanisms. The phosphorothioate nucleic acid, phosphorothioate polymer backbone or non-cell penetrating protein can be covalently or non-covalently attached to the biotin-binding domain or the biotin domain. The non-cell penetrating protein may be covalently bound to a biotin-binding domain or a biotin domain. Where the non-cell penetrating protein is covalently bound to a biotin-binding domain or biotin domain, the biotin-binding domain or biotin domain covalently binds an amino acid of the protein. In embodiments, the non-cell penetrating protein includes a covalent reactive moiety (as described above) and the reactive moiety is reactive with the biotin-binding domain or the biotin domain. In embodiments, the biotin-binding domain or the biotin domain includes a covalent reactive moiety and the reactive moiety is reactive with the non-cell penetrating protein.

In embodiments, the phosphorothioate nucleic acid or phosphorothioate polymer backbone includes a covalent reactive moiety and the reactive moiety is reactive with the biotin-binding domain or the biotin domain. As described above, the covalent reactive moiety may be reactive with a lysine, arginine, cysteine or histidine of the protein (e.g. with the amino acid side chains). In embodiments, the covalent reactive moiety is reactive with a cysteine. The covalent reactive moiety may be a vinyl sulfone. In embodiments, phosphorothioate nucleic acid or phosphorothioate polymer backbone includes a reactive moiety having the formula S—S—R, where R is a protecting group. In embodiments, R is a hexanol (a monovalent substituent). As used herein, the term hexanol includes compounds with the formula $C_6H_{13}OH$ and includes, 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 2,2-dimethyl-1-butanol, 2,3-dimethyl-1-butanol, 3,3-dimethyl-1-butanol, 2,3-dimethyl-2-butanol, 3,3-dimethyl-2-butanol, and 2-ethyl-1-butanol. In embodiments, R is 1-hexanol. In embodiments, the phosphorothioate nucleic acid is covalently bound to the biotin-binding domain or biotin domain. In embodiments, the phosphorothioate nucleic acid includes a reactive moiety. In embodiments, the reactive moiety is a vinyl sulfone or a reactive moiety with the formula S—S—R, as described above. In embodiments, R is a hexanol, for example, 1-hexanol.

In embodiments, when a plurality of phosphorothioate nucleic acids or phosphorothioate polymer backbones are attached to the biotin-binding domain or biotin domain, each of the plurality can be covalently or non-covalently attached. In embodiments, when a plurality of biotin-binding domains or biotin domains are attached to the non-cell penetrating protein, each of the plurality can be covalently or non-covalently attached. The phosphorothioate nucleic acids, phosphorothioate polymer backbones or non-cell penetrating protein may contain a reactive moiety, e.g., an amino acid reactive moiety or covalent reactive moiety, that facilitates attachment of the phosphorothioate nucleic acid, phosphorothioate polymer backbone or non-cell penetrating protein to the biotin-binding domain or the biotin domain. Thus, the phosphorothioate nucleic acids, phosphorothioate polymer backbones or non-cell penetrating protein can be attached to the biotin-binding domain or the biotin domain through a reactive moiety as described herein.

Provided are a plurality of cell penetrating conjugates including non-cell penetrating proteins attached to phosphosphorothioate nucleic acids or phosphorothioate polymer backbones through a non-covalent linker including a biotin-binding domain (e.g., avidin or streptavidin) non-covalently bound to a biotin domain. The phosphorothioate nucleic acids or phosphorothioate polymer backbones are covalently or non-covalently attached to the biotin-binding domain or biotin domain of the non-covalent linker. In embodiments, the plurality includes phosphorothioate nucleic acids or phosphorothioate polymer backbones covalently attached to a biotin-binding domain or biotin domain and does not include biotin-binding domains or biotin domains with non-covalently attached phosphorothioate nucleic acids or phosphorothioate polymer backbones. In embodiments, the phosphorothioate nucleic acids or phosphorothioate polymer backbones are non-covalently attached to the biotin-binding domain or biotin domain and the plurality does not include biotin-binding domains or biotin domains with covalently attached phosphorothioate nucleic acids or phosphorothioate polymer backbones. In some embodiments, the plurality includes one or more of the biotin-binding domains or biotin domains including non-covalently attached phosphorothioate nucleic acids or phosphorothioate polymer backbones and one or more one or more of the biotin-binding domains or biotin domains including covalently attached phosphorothioate nucleic acids or phosphorothioate polymer backbones. Thus, the plurality can include biotin-binding domains or biotin domains including non-covalently and covalently attached phosphorothioate nucleic acids or phosphorothioate polymer backbones.

In embodiments, the phosphorothioate nucleic acid or phosphorothioate polymer backbone is about 10, 20, 30, 40, 50, 60, 70, 80, 90, 100 or more nucleic acid residues in length. In embodiments, the phosphorothioate nucleic acid or phosphorothioate polymer backbone is from about 10 to about 30 nucleic acid residues in length. In embodiments, the phosphorothioate nucleic acid or phosphorothioate polymer backbone acid is about 20 nucleic acid residues in length. In embodiments, the length of each nucleic acid or polymer backbone can be at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleic acid residues or sugar residues in length. In embodiments, each phosphorothioate nucleic acid or phosphorothioate polymer backbone is independently from 5 to 50, 10 to 50, 15 to 50, 20 to 50, 25 to 50, 30 to 50, 35 to 50, 40 to 50, 45 to 50, 5 to 75, 10 to 75, 15 to 75, 20 to 75, 25 to 75, 30 to 75, 35 to 75, 40 to 75, 45 to 75, 50 to 75, 55 to 75, 60 to 75, 65 to 75, 70 to 75, 5 to 100, 10 to 100, 15 to 100, 20 to 100, 25 to 100, 30 to 100, 35 to 100, 40 to 100, 45 to 100, 50 to 100, 55 to 100, 60 to 100, 65 to 100, 70 to 100, 75 to 100, 80 to 100, 85 to 100, 90 to 100, 95 to 100, or more residues in length. In embodiments, each phosphorothioate nucleic acid or phosphorothioate polymer backbone is independently from 10 to 15, 10 to 20, 10 to 30, 10 to 40, or 10 to 50 residues in length.

In embodiments, the length of one phosphorothioate nucleic acid or phosphorothioate polymer backbone differs from another phosphorothioate nucleic acid or phosphorothioate polymer backbone. By way of example, if two phosphorothioate nucleic acids or phosphorothioate polymer backbones are attached to a non-cell penetrating protein through a non-covalent linker the first phosphorothioate nucleic acid or phosphorothioate polymer backbone can be of one length (e.g., 22 residues) and the second phosphorothioate nucleic acid or phosphorothioate polymer backbone can be of a different length (e.g. 25 residues). Thus, if a plurality of phosphorothioate nucleic acids and phosphorothioate polymer backbones are attached through a non-covalent linker to a non-cell penetrating protein, the phosphorothioate nucleic acids and phosphorothioate polymer backbones can have a number of different lengths, e.g., ranging from 10 to 30 residues in length.

In embodiments, a plurality of phosphorothioate nucleic acids or phosphorothioate polymer backbones are attached to the non-cell penetrating protein through a plurality of non-covalent linkers including a biotin-binding domain non-covalently bound to a biotin domain. In embodiments, 1, 2, 3, 4, 5, 6, 7, 8, 9, 10, 15, 20, 25, or more phosphorothioate nucleic acids or phosphorothioate polymer backbones are attached to the protein. In embodiments, a plurality of phosphorothioate nucleic acids or phosphorothioate polymer backbones are attached to the biotin-binding domain or biotin domain of the non-covalent linker. In embodiments, 1, 2, 3, 4, 5, 6, 7, 8, 9, 10, 15, 20, 25, or more phosphorothioate nucleic acids or phosphorothioate polymer backbones are attached to the biotin-binding domain or biotin domain of the non-covalent linker. In embodiments, a plurality of biotin-binding domains or biotin domains are attached to the protein. In embodiments, 1, 2, 3, 4, 5, 6, 7, 8, 9, 10, 15, 20, 25, or more biotin-binding domains or biotin domains are attached to the protein.

In embodiments, the non-cell penetrating protein has a molecular weight of more than 25 kD. In embodiments, the non-cell penetrating protein has a molecular weight of about 25 kD to about 750 kD. Thus, the non-cell penetrating protein can have a molecular weight of at least about 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, or more kilodaltons (kD). In embodiments, the non-cell penetrating protein has a molecular weight from at least about 25 to 100 kD, at least about 25 to 150 kD, at least about 25 to 200 kD, at least about 25 to 250 kD, at least about 25 to 300 kD, at least about 25 to 350 kD, at least about 25 to 400 kD, at least about 25 to 450 kD, at least about 25 to 500 kD, at least about 25 to 550 kD, at least about 25 to 600 kD, at least about 25 to 650 kD, at least about 25 to 700 kD or at least above 25 to 750 kD.

In embodiments, the non-cell penetrating protein is an antibody. As discussed in more detail above, antibodies can be full length antibodies such as IgG, IgA, IgM, IgD or IgE antibodies or fragments thereof. In embodiments, the antibody is an IgG antibody or a fragment thereof. In embodiments, the antibody is an IgG antibody or a fragment thereof. In embodiments, the antibody is an Fv fragment or a humanized antibody. In embodiments, the antibody is an IgA, IgM, IgD or IgE antibody. In embodiments, the antibody is an Fv fragment. In embodiments, the antibody is a humanized antibody. Thus, provided are antibodies attached to a phosphorothioate nucleic acid or polymer backbone through a non-covalent linker including a biotin-binding domain and a biotin domain, wherein the phosphorothioate nucleic acid or polymer backbone enhances delivery of the antibody into a cell. In embodiments, the antibody is a therapeutic antibody, i.e., an antibody used in the treatment of disease. Thus, also provided are therapeutic antibodies attached to one or more phosphorothioate nucleic acids or polymer backbones wherein the antibody binds an intracellular target.

In embodiments, the non-cell penetrating protein binds an intracellular target. The intracellular target can be a therapeutic target or a diagnostic target or other target of interest located intracellularly, e.g., a target or structure, e.g., histone, to be imaged, e.g., by confocal microscopy. Thus, provided are cell penetrating conjugates bound to an intracellular target. In embodiments, the intracellular target is a target of a disease selected from the group consisting of autoimmune disease, inflammatory disease, metabolic disorder, developmental disorder, cardiovascular disease, liver disease, intestinal disease, infectious disease, endocrine disease, neurological disorder, and cancer. Examples of intracellular targets include without limitation oncogenic transcription factors including but not limited to STAT3, Myc, NFκB, AP1, HIF, mutant p53; oncoproteins including but not limited to Ras, Raf, MAPK, PI3 kinase, AKT, BTK, JAKs, SRC family members; immunomodulatory molecules including FOXp3, T-BET, GATA3, STAT1, 2, 3, 4, 5, 6. The target of a disease can be a diagnostic target or therapeutic target or other target of interest associated with the disease. Exemplary intracellular targets of cancer include, but are not limited to, STAT (e.g., STAT3), NFκB, PKB/Akt, Myc family members, steroid hormone receptors (e.g., estrogen receptor), ligands of steroid hormone receptors (e.g., cyclin D1), receptor tyrosine kinases (RTKs), EGFR, VEGFR, PDGFR, Src family members, Ras, Abl, BCR-Abl, NPM-Alk, Janus kinases (JAKs), Brutun's tyrosine kinase (BTK), and viral oncoproteins (e.g., an EBV protein, or an HPV protein, e.g., E6 and E7). In embodiments, the intracellular target of the infectious disease is a viral protein or viral transcript. Thus, the intracellular target can be a viral protein or viral transcript of a human immunodeficiency virus (HIV), influenza virus, herpes simplex cirus, epstein barr virus, cytomegalovirus, human papilloma virus, or hepatitis virus. In embodiments, the intraceullar target is a DNA binding protein including, but not limited to, a transcription factor, a transcriptional enhancer, a transcriptional repressor, a histone or post-translationally modified histone. In embodiments, the intracellular target is epigenetically modified DNA, e.g., methylated or hydroxymethylated cytosine (5mC or 5hmC), 5-formylcytosine (5fC) and 5-carboxylcytosine (5caC). In embodiments, the intracellular target is a nucleic acid, e.g., an RNA transcript or a nucleic acid. For example, the intracellular target may be the nucleic acid of an infectious pathogen, e.g., a parasite, virus or bacteria. In embodiments, the intracellular target is a signaling molecule or a transcription factor. In embodiments, the signaling molecule is a phosphatase or kinase. In embodiments, the intracellular target is a cancer target or located within a cancer cell. In embodiments, the intracellular target is a STAT, e.g., STAT3 or exportin 7. In embodiments, the intracellular target is selected from the group consisting of STAT3, exportin 7 and Src. In embodiments, the intracellular target is phosphorylated Src. In embodiments, the intracellular target is FOXp3. In embodiments, the intracellular target is T-BET. In embodiments, the non-cell penetrating protein further comprises a label, a small molecule or a functional nucleic acid attached to the protein. In embodiments, the cell penetrating conjugate is bound to an intracellular target.

Cell Compositions

In another aspect, a cell including the cell penetrating conjugate provided herein including embodiments thereof is provided. Provided are cells including one or more of the provided cell penetrating conjugates, e.g., the cells may include a plurality of cell penetrating conjugates. In embodiments, the cell is a cancer cell. In embodiments, the cell is a non-cancer cell. In embodiments, the cell is a T cell. In embodiments, the cell is a regulatory T cell. In embodiments, the conjugate is bound within the cell to an intracellular target. By way of example, the cells can include a first non-cell penetrating protein and a second non-cell penetrating protein attached to one or more phosphorothioate nucleic acids or polymer backbones through a non-covalent linker including a biotin-binding domain non-covalently bound to a biotin domain. The first and second non-cell penetrating protein may be bound within the cell to an intracellular target. In embodiments, the second non-cell penetrating protein binds a different epitope on the intracellular target relative to the first non-cell penetrating protein. In embodiments, the second non-cell penetrating protein binds a second intracellular target. In embodiments, the first and/or second non-cell penetrating protein is an antibody. Thus, the first and second non-cell penetrating proteins can be the same protein or a different protein.

Pharmaceutical Compositions

Provided herein are pharmaceutical compositions comprising the cell penetrating conjugates and a pharmaceutically acceptable carrier. The provided compositions are, inter alia, suitable for formulation and administration in vitro or in vivo. Suitable carriers and excipients and their formulations are described in Remington: The Science and Practice of Pharmacy, 21st Edition, David B. Troy, ed., Lippicott Williams & Wilkins (2005). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject.

Pharmaceutical compositions provided by the present invention include compositions wherein the active ingredient (e.g. compositions described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, the recombinant proteins described herein will contain an amount of active ingredient effective to achieve the desired result, e.g., modulating the activity of a target molecule, and/or reducing, eliminating, or slowing the progression of disease symptoms. Determination of a therapeutically effective amount of a compound of the invention is well within the capabilities of those skilled in the art, especially in light of the detailed disclosure herein.

In another aspect, a pharmaceutical composition including the cell penetrating conjugate provided herein including embodiments thereof and a pharmaceutically acceptable carrier is provided. In embodiments, the pharmaceutical composition further includes a second non-cell penetrating protein including a second non-covalent linker attaching one or more phosphorothioate nucleic acids to the second non-cell penetrating protein. In embodiments, the non-covalent linker includes a biotin-binding domain non-covalently attached to a biotin domain. In embodiments, the second non-cell penetrating protein binds an intracellular target. In embodiments, the second non-cell penetrating protein binds a different epitope on the intracellular target relative to the non-cell penetrating protein provided herein including embodiments thereof. In embodiments, the second non-cell penetrating protein binds a second intracellular target. In embodiments, the second non-cell penetrating protein is an antibody.

Provided compositions can include a single agent or more than one agent. In some embodiments, the compositions further include a second non-cell penetrating protein attached to one or more phosphorothioate nucleic acids or polymer backbones through a non-covalent linker including a biotin-binding domain non-covalently bound to a biotin domain. Thus, provided herein are compositions including a first cell-penetrating conjugate including a first non-cell penetrating protein attached to one or more phosphorothioate nucleic acids or polymer backbones through a first non-covalent linker including a first biotin-binding domain non-covalently bound to a first biotin domain and a second cell-penetrating conjugate including a second non-cell penetrating protein attached to one or more phosphorothioate nucleic acids or polymer backbones through a second non-covalent linker including a second biotin-binding domain non-covalently bound to a second biotin domain. In embodiments, the second non-cell penetrating protein binds an intracellular target. In embodiments, the second non-cell penetrating protein binds a different epitope on the intracellular target relative to the first non-cell penetrating protein. In embodiments, the second non-cell penetrating protein binds a second intracellular target. In embodiments, the first and/or second non-cell penetrating protein is an antibody. The first and second non-cell penetrating proteins can be the same protein or a different protein.

The compositions for administration will commonly include an agent as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In some embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the active compounds or constructs in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

The formulations of compounds can be presented in unit-dose or multi-dose sealed containers, such as ampules and vials. Thus, the composition can be in unit dosage form. In such form the preparation is subdivided into unit doses containing appropriate quantities of the active component. Thus, the compositions can be administered in a variety of unit dosage forms depending upon the method of administration. For example, unit dosage forms suitable for oral administration include, but are not limited to, powder, tablets, pills, capsules and lozenges.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer and severity of such symptoms), kind of concurrent treatment, complications from the disease being treated or other health-related problems. Other therapeutic regimens or agents can be used in conjunction with the methods and compounds of the invention. Adjustment and manipulation of established dosages (e.g., frequency and duration) are well within the ability of those skilled in the art.

For any composition (e.g., the cell-penetrating conjugate provided) described herein, the therapeutically effective amount can be initially determined from cell culture assays. Target concentrations will be those concentrations of active compound(s) that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred "Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Methods of Forming Conjugates

In another aspect, a method of forming a cell penetrating conjugate is provided. The method includes contacting a non-cell penetrating protein with a phosphorothioate nucleic acid, wherein the non-cell penetrating protein is attached to a first member of a biotin binding pair and the phosphorothioate nucleic acid is attached to a second member of the biotin binding pair, thereby forming a cell penetrating conjugate, which includes a non-covalent bond between a biotin domain and biotin-binding domain. As described above, the first member of a biotin binding pair may be a biotin-binding domain or a biotin domain and the second member of a biotin binding pair may be a biotin-binding domain or a biotin domain. In embodiments, the first member of the biotin binding pair is a biotin-binding domain. In embodiments, the second member of the biotin binding pair is a biotin domain. In embodiments, the first member of the biotin binding pair is a biotin domain. In embodiments, the second member of the biotin binding pair is a biotin-binding domain. In embodiments, the phosphorothioate nucleic acid includes a covalent reactive moiety. In embodiments, the biotin-binding domain non-covalently bound to the biotin domain form a non-covalent linker.

Methods of Delivery

In another aspect, a method of delivering a non-cell penetrating protein into a cell is provided. The method includes contacting the cell with the cell penetrating conjugate as provided herein including embodiments thereof. In embodiments, the non-cell penetrating protein binds the nuclear protein in the cytoplasm thereby forming a non-cell penetrating protein-nuclear protein complex. In embodiments, the non-cell penetrating protein-nuclear protein complex is not capable of entering the nucleus of the cell.

In embodiments, the cell penetrating conjugates are used for diagnosing a disease in a subject. Thus, provided is a method of diagnosing a disease in a subject comprising administering to the subject an effective amount of a cell penetrating conjugate or composition comprising a cell penetrating conjugate as described herein. Administration of the conjugate diagnoses the disease or one or more symptoms of the disease in the subject. The disclosed methods involve comparing the levels or activity of a biomarker, e.g., intracellular target of a disease, from a test sample to a control sample. As discussed above, a control sample or value refers to a sample that serves as a reference, usually a known reference, for comparison to a test sample. A control can also represent an average value gathered from a population of similar individuals, e.g., cancer patients or healthy individuals with a similar medical background, same age, weight, etc. A control value can also be obtained from the same individual, e.g., from an earlier-obtained sample, prior to disease, or prior to treatment. As also discussed above, diagnosis refers to a relative probability that a disease (e.g. an autoimmune, inflammatory autoimmune, cancer, infectious, immune, or other disease) is present in the subject.

The terms comparing, correlating and associated, in reference to determination of a disease risk factor, refers to comparing the presence or amount of the risk factor (e.g., amount of intracellular target of a disease) in an individual to its presence or amount in persons known to suffer from, or known to be at risk of disease, or in persons known to be free of disease, and assigning an increased or decreased probability of having/developing the disease to an individual based on the assay result(s).

Methods of Detecting

Provided herein is also a method of detecting an intracellular target in a cell, including contacting the cell with a cell penetrating conjugate as provided herein including embodiments thereof and detecting binding of the cell penetrating conjugate to the intracellular target. The cell can be a fixed cell or a live cell. In embodiments, the cell is located in vitro or in vivo. Binding can be detecting directly or indirectly. It is understood and contemplated herein that numerous methods may be used to detect the binding of the cell penetrating conjugate to its intracellular target. For example, binding can be detected directly by assaying coupling between the cell penetrating conjugate and its intracellular target. Binding can be determined, for example, by selecting an assay from the group consisting of a coimmunoprecipitation assay, a colocalization assay, or a fluorescence polarizing assay, as described below. The assays are known in the art, e.g., see Sambrook et al., Molecular Cloning: A Laboratory Manual, $3^{rd}$ Ed., Cold Spring Harbor Press, Cold Spring Harbor, N.Y. (2001); Dickson, Methods Mol. Biol. 461:735-44 (2008); Nickels, Methods 47(1):53-62 (2009); and Zinchuk et al., Acta Histochem. Cytochem. 40(4):101-11 (2007).

In embodiments, binding is determining by an imaging method or system. Thus, the cell penetrating conjugates provided herein including embodiments thereof can also be used in imaging applications or other applications for analyzing intracellular target levels and/or activities. For example, the provided cell penetrating conjugates can be used for in vitro or in vivo imaging of intracellular targets of interest. In embodiments, the cell penetrating conjugates are used for live cell imaging. For example, live cell imaging can be used to monitor intracellular target distribution and/or dynamics inside living cells and is also applicable to monitoring target interactions. For example, the cell penetrating conjugates can be used in immunoprecipitation and co-immunoprecipitation assays to study protein-protein interactions in cells, In embodiments, in living cells. In embodiments, the cell penetrating conjugates are used for analysis of intracellular targets by flow cytometry. In imaging applications, the cell penetrating conjugates are, In embodiments, labeled as appropriate to the application being used. As described above, a label or a detectable moiety is a composition detectable by spectroscopic, photochemical, biochemical, immunochemical, chemical, or other physical means. Useful labels include, but are not limited to, 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, Bioconjugate Techniques 1996, Academic Press, Inc., San Diego.

Methods of Treatment

The cell penetrating conjugates provided herein including embodiments thereof and compositions including the cell penetrating conjugates as described herein including embodiments thereof are useful for both prophylactic and therapeutic treatment. For prophylactic use, a therapeutically effective amount of the agents described herein are administered to a subject prior to or during early onset (e.g., upon initial signs and symptoms of an autoimmune disease). Therapeutic treatment involves administering to a subject a therapeutically effective amount of the agents described herein after diagnosis or development of disease. Thus, in another aspect, a method of treating a disease in a subject in need thereof is provided. The method includes administering to a subject an effective amount of the cell penetrating conjugate as provided herein including embodiments thereof, thereby threating the disease in the subject.

In embodiments, the method includes administering to the subject a second non-cell penetrating protein including a second non-covalent linker attaching one or more phosphorothioate nucleic acids to the second non-cell penetrating protein. In embodiments, the non-covalent linker includes a biotin-binding domain non-covalently attached to a biotin domain. In embodiments, the second non-cell penetrating protein binds a different epitope on the intracellular target relative to the conjugate provided herein including embodiments thereof. In embodiments, the second non-cell penetrating protein binds a second intracellular target. In embodiments, the conjugate provided herein including embodiments thereof and the second non-cell penetrating protein are administered simultaneously. In embodiments, the conjugate provided herein including embodiments thereof and the second non-cell penetrating protein are administered sequentially.

In embodiments, the second non-cell penetrating protein is an antibody. In embodiments, the method includes administering a second therapeutic agent to the subject. In embodiments, the disease is selected from the group consisting of autoimmune disease, developmental disorder, inflammatory disease, metabolic disorder, cardiovascular disease, liver disease, intestinal disease, infectious disease, endocrine disease, neurological disorder, and cancer. In embodiments, the disease is an autoimmune disease. In embodiments, the disease is a developmental disorder. In embodiments, the disease is an inflammatory disease. In embodiments, the disease is a metabolic disorder. In embodiments, the disease is a cardiovascular disease. In embodiments, the disease is a liver disease. In embodiments, the disease is an intestinal disease. In embodiments, the disease is an infectious disease. In embodiments, the disease is an endocrine disease. In embodiments, the disease is a neurological disorder. In embodiments, the disease is cancer. In embodiments, the non-cell penetrating protein of the conjugate binds an intracellular target and the intracellular target is STAT3, exportin 7, or Src. In embodiments, the non-cell penetrating protein of the conjugate binds an intracellular target and the intracellular target is phosphorylated Src. In embodiments, the non-cell penetrating protein of the conjugate is an antibody that specifically binds STAT3 and the second non-cell penetrating protein is an antibody that specifically binds exportin 7. In embodiments, the non-cell penetrating protein of the conjugate is an antibody that specifically binds STAT3 and the second non-cell penetrating protein is an antibody that specifically binds another epitope of STAT3.

In the provided methods of treatment, additional therapeutic agents can be used that are suitable to the disease being treated. Thus, in some embodiments, the provided methods of treatment further comprise administering a second therapeutic agent to the subject. Suitable additional therapeutic agents include, but are not limited to, therapeutic agent is selected from the group consisting of analgesics, anesthetics, analeptics, corticosteroids, anticholinergic agents, anticholinesterases, anticonvulsants, antineoplastic agents, allosteric inhibitors, anabolic steroids, antirheumatic agents, psychotherapeutic agents, neural blocking agents, anti-inflammatory agents, antihelmintics, antibiotics, anticoagulants, antifungals, antihistamines, antimuscarinic agents, antimycobacterial agents, antiprotozoal agents, antiviral agents, dopaminergics, hematological agents, immunological agents, muscarinics, protease inhibitors, vitamins, growth factors, and hormones. The choice of agent and dosage can be determined readily by one of skill in the art based on the given disease being treated.

Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions. The course of treatment is best determined on an individual basis depending on the particular characteristics of the subject and the type of treatment selected. The treatment, such as those disclosed herein, can be administered to the subject on a daily, twice daily, bi-weekly, monthly or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly).

According to the methods provided herein, the subject is administered an effective amount of one or more of the agents provided herein. The terms effective amount and effective dosage are used interchangeably. The term effective amount is defined as any amount necessary to produce a desired physiologic response (e.g., reduction of inflammation). Effective amounts and schedules for administering the agent may be determined empirically by one skilled in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)).

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

The terms "subject," "patient," "individual," etc. are not intended to be limiting and can be generally interchanged. That is, an individual described as a "patient" does not necessarily have a given disease, but may be merely seeking medical advice.

As used herein, "treating" or "treatment of" a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean prolonging survival of a subject beyond that expected in the absence of treatment. "Treating" can also mean inhibiting the progression of the condition, disorder or disease, slowing the progression of the condition, disorder or disease temporarily, although in some instances, it involves halting the progression of the condition, disorder or disease permanently. As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

Where combination treatments are contemplated, it is not intended that the agents (i.e. ribonucleic acid compounds) described herein be limited by the particular nature of the combination. For example, the agents described herein may be administered in combination as simple mixtures as well as chemical hybrids. An example of the latter is where the agent is covalently linked to a targeting carrier or to an active pharmaceutical. Covalent binding can be accomplished in many ways, such as, though not limited to, the use of a commercially available cross-linking agent.

As used herein, the term "pharmaceutically acceptable" is used synonymously with "physiologically acceptable" and "pharmacologically acceptable". A pharmaceutical composition will generally comprise agents for buffering and preservation in storage, and can include buffers and carriers for appropriate delivery, depending on the route of administration.

An "effective amount" is an amount sufficient to accomplish a stated purpose (e.g. achieve the effect for which it is administered, treat a disease, reduce enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein relative to the absence of the antagonist. A "function disrupting amount," as used herein, refers to the amount of antagonist required to disrupt the function of an enzyme or protein relative to the absence of the antagonist. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In embodiments, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

Kits

In another aspect, a kit including the cell penetrating conjugate provided herein including embodiments thereof or the pharmaceutical composition as provided herein including embodiments thereof and instructions for use are provided. In embodiments, the kit includes a second non-cell penetrating protein including a second non-covalent linker attaching one or more phosphorothioate nucleic acids to the second non-cell penetrating protein. In embodiments, the second non-covalent linker includes a second biotin-binding domain non-covalently bound to a second biotin domain. In embodiments, the conjugate provided herein including embodiments thereof and the second non-cell penetrating protein are in separate containers. In embodiments, the second non-cell penetrating protein binds a different epitope on the intracellular target relative to the non-cell penetrating protein provided herein including embodiments thereof. In embodiments, the second non-cell penetrating protein binds a second intracellular target. In embodiments, the second non-cell penetrating protein is formulated as a pharmaceutical composition including a second non-cell penetrating protein and a pharmaceutically acceptable carrier. In embodiments, the second non-cell penetrating protein is an antibody. In embodiments, the kit includes one or more additional agents for treating or preventing one or more symptoms of a disease. In embodiments, the kit includes a means of administering the composition, such as, for example, a syringe, needle, tubing, catheter, patch, and the like. The kit may also include formulations and/or materials requiring sterilization and/or dilution prior to use.

EXAMPLES

Example 1

Applicants demonstrate that phosporothioated (PS) DNA oligomers at a 20mer length enable antibodies to penetrate into live cells and recognize intended antigen. Phosphorothioation occurs in the sugarphosphate backbone of DNA oligos. Applicants demonstrate that attachment of PS DNA oligos facilitates antibody intracellular delivery as well as target recognition efficiently, with 20mer PS DNA oligos being very efficient. Conjugation with PEGylation, 2'fluoro-, 2'methylA-, or 2'methylG-modification of the DNA oligos does not facilitate antibody intracellular uptake and attachment of PS RNA oligos does not facilitate intracellular delivery. DNA oligos with various modifications mentioned above, and RNA (20mer) with PS modification, were synthesized with biotin attached; antibodies were labeled with avidin/streptavidin to enable non-covalent linkage of oligos with antibodies.

The methods and compositions provided are useful for the purification of the cell-penetrating conjugates provided herein including embodiments thereof. The attached non-covalent linker including the biotin-binding domain non-covalently bound to the biotin domains causes an increase in the molecular weight of the conjugate relative to the absence of the non-covalent linker. Therefore, the conjugates provided herein can be conveniently purified using standard size exclusions methodology commonly known in the art.

Structure

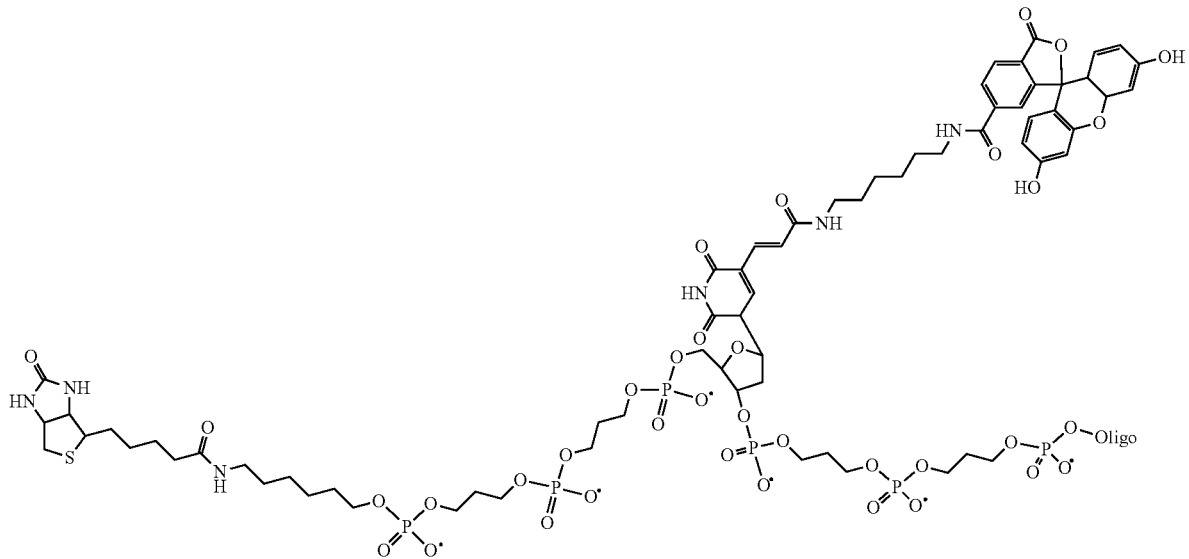

5'-Biotin oligo: red = biotin, black = C3 and green = fluorescein dT units

Figure 4A:
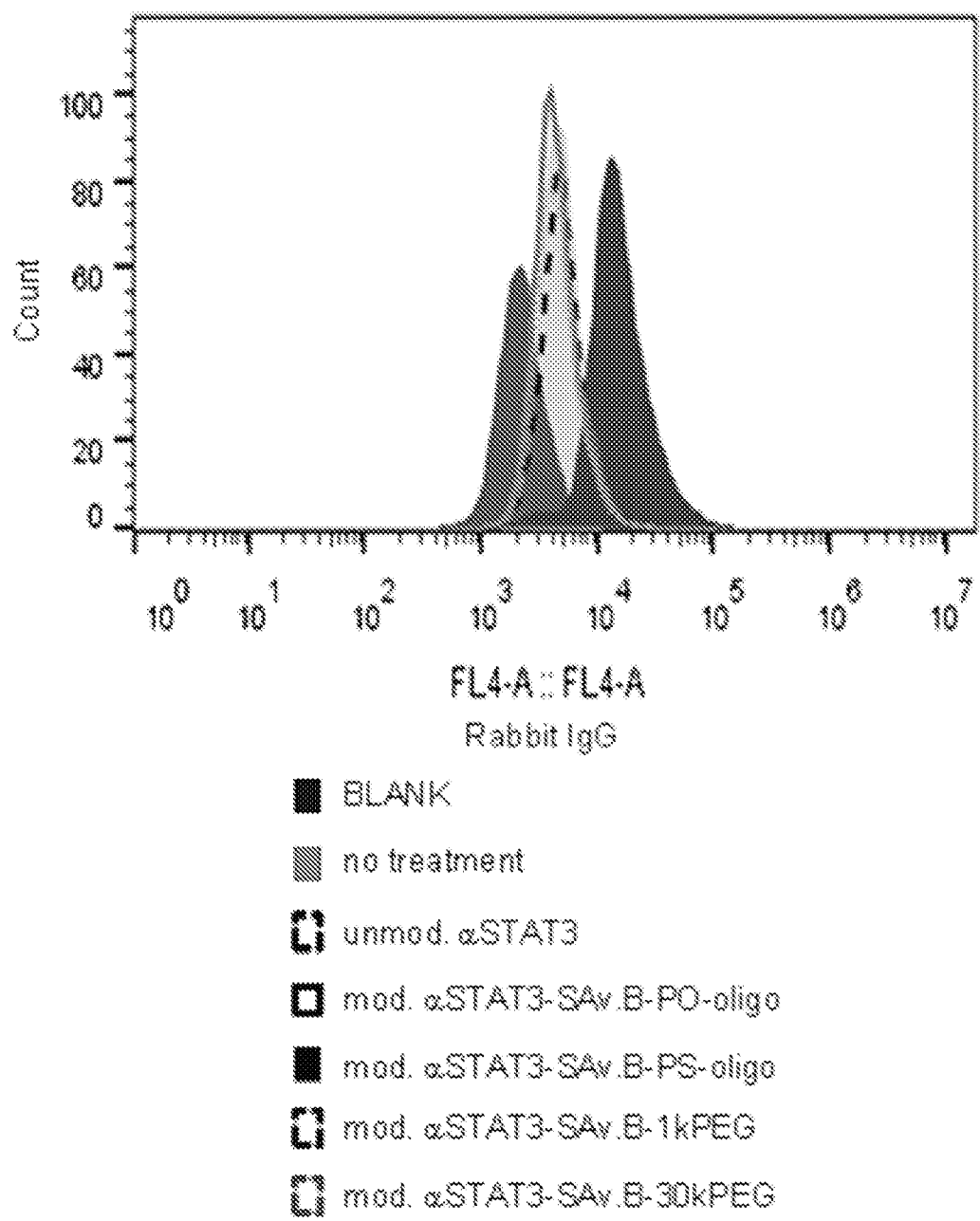
FIG. 4A and FIG. 4B: Direct comparison of attachment of phosphorothioated DNA-oligo vs PEGylation to antibody protein via biotin-avidin/streptavidin for cell penetration and intracellular target recognition. Non-covalent linkage of DNA-oligo's via avidin-biotin to antibody protein is superior to antibody PEGylation. Human glioma U251 cells were incubated with anti-STAT3 antibodies (rabbit) modified as indicated for 1 h at 10 mg/ml.

Modified anti-STAT3 antibodies conjugated to PS-DNA oligo via Streptavidin/Biotin are capable of cell-penetration. FIG. 4A shows Flow cytometry analysis to detect delivered antibodies, the antibody-antigen complex, using a secondary antibody. U251 cells (human glioma stem cells) were treated with modified anti-STAT3 antibodies conjugated to PO-DNA oligo (20mer) (red line), PS-DNA oligo (20mer) (red area), 1kPEG (blue line) and 30kPEG (dashed line) via Streptavidin/Biotin. The U251 cells were treated with 10 µg/ml of the particular modified anti-STAT3 antibody and were incubated for one hour at 37° C. After a washing step (PBS/1% BSA), the cells were harvested and fixed with 500 µl 2% paraformaldehyde (15 min.) followed by a washing step (PBS/1% BSA) and proceeded by 500 ice-cold methanol (10 min.). After washing (PBS/1% BSA) the cells were blocked with PBS/1% BSA/1% mouse serum for one hour at 4° C. Afterwards the cells were washed (PBS/1% BSA) and stained with a secondary antibody (anti-rabbit AF647 1:4.000 in PBS) for 30 min. in the dark. The flow analysis was performed after three final washing steps (PBS/1% BSA) and collecting the cells in 300 µl of washing buffer. Unstained U251 were used as a blank control (grey area).

Figure 4B:
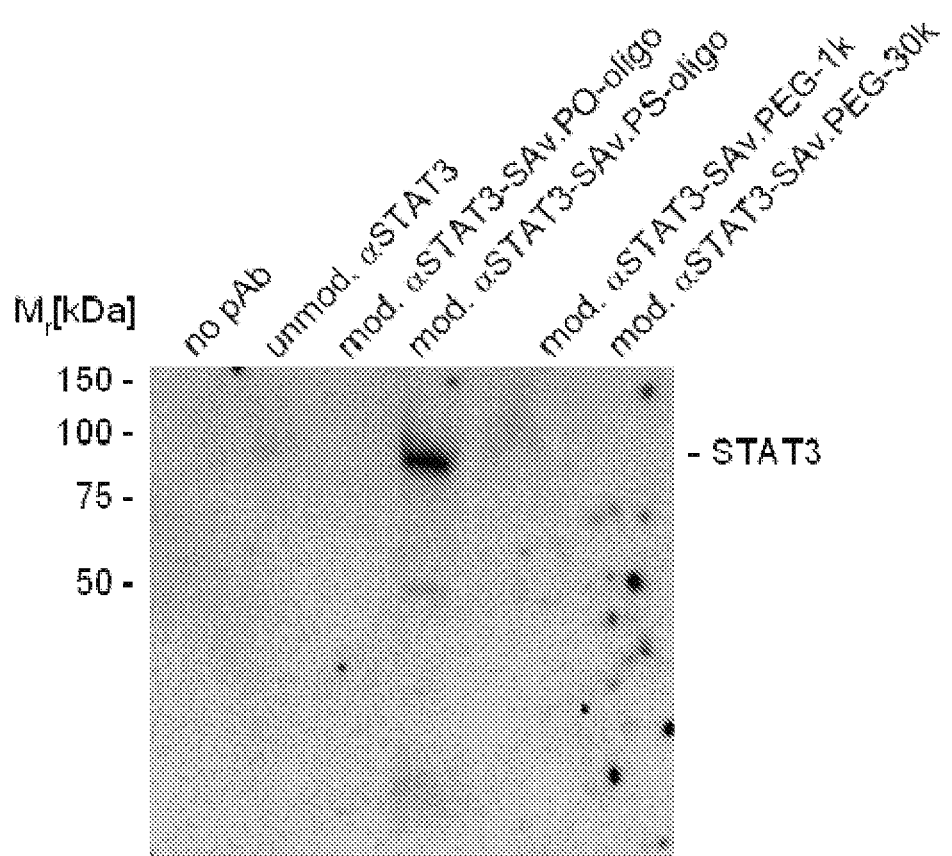
Figure 5A:
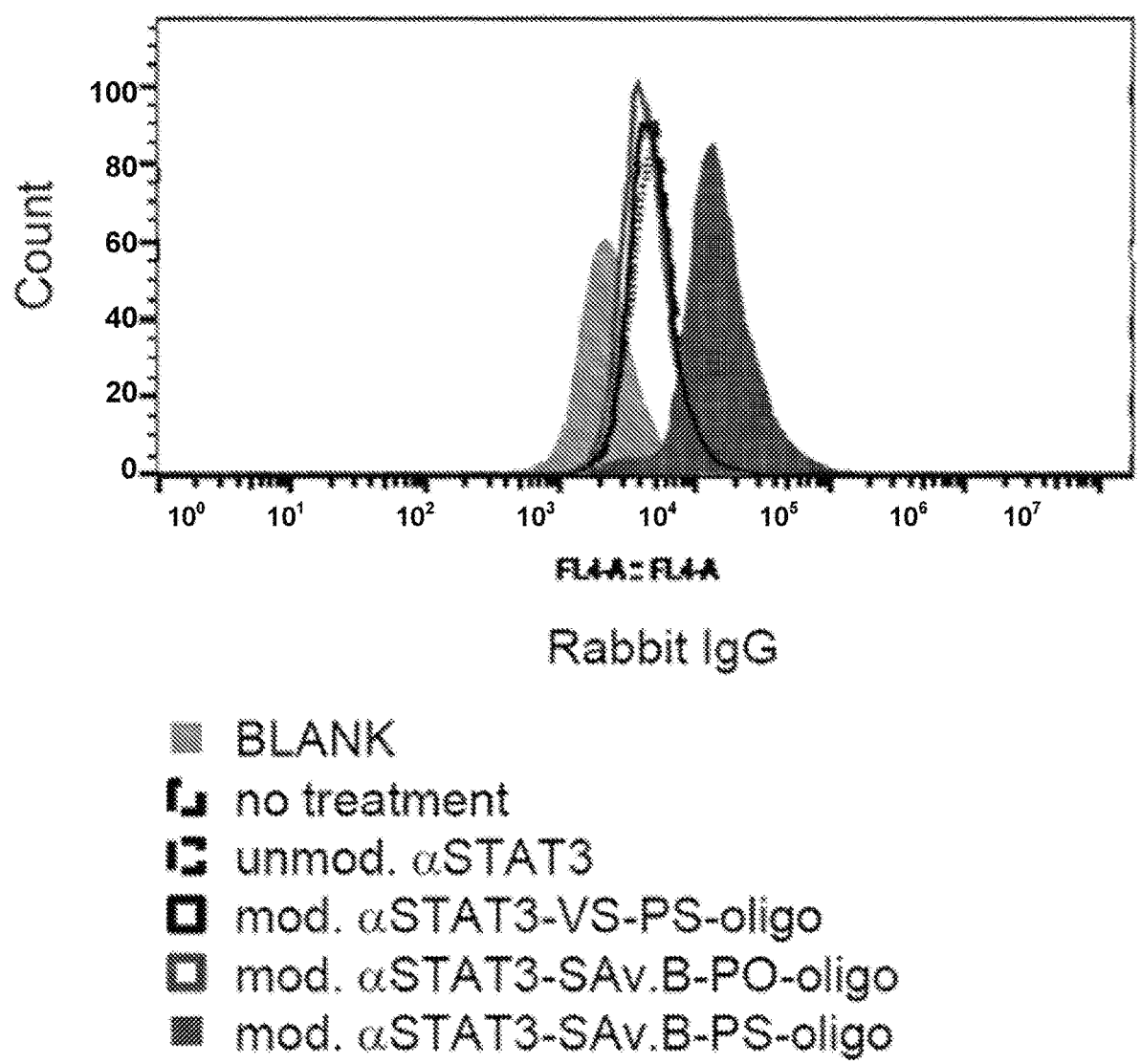
FIG. 5A and FIG. 5B: Non-covalent linkage of DNA-oligo's to antibody Non DNA oligo s protein is superior to covalent linkage driven by vinyl sulfone chemistry. 10 µg/ml antibodies as indicated were incubated for 1 h with U251 cells (A, 6 well plate; BC, 12 well plate), washed with PBS and lysates were prepared; agarose beads were added to cleared lysates and WB was performed.
Figure 5B:
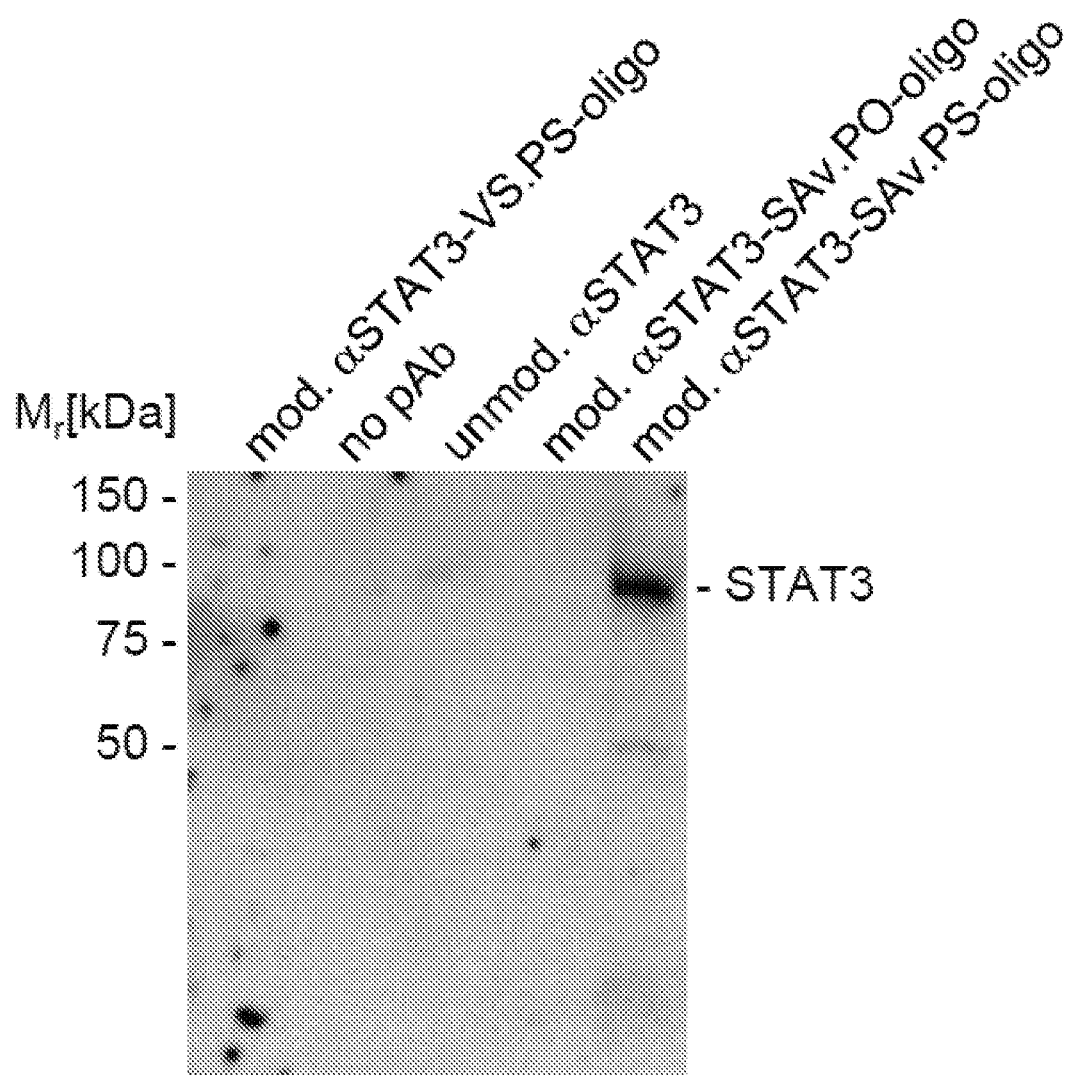

FIG. 4B shows alternative Western blotting analysis to detect delivered antibody-antigen complex. U251 cells were treated with modified anti-STAT3 antibodies conjugated to PO-DNA oligo (20mer) (first lane), PS-DNA oligo (20mer) (second lane), PEG-1k-DNA oligo (third lane) and PEG-30k-DNA oligo (fourth lane) via Streptavidin/Biotin. The U251 cells were treated with 10 µl g/ml of the indicated modified anti-STAT3 antibody and were incubated for one hour at 37° C. After the incubation and two washing steps with PBS (2 ml) the cells were lysed via incubation (30 min.) on ice in 500 µl RIPA buffer, followed by vigorous vortexing. The full cell lysates were harvested by collecting the supernatant after a centrifugation step (10 min. 13.000 rpm, 4° C.). To each full cell lysate 30 µl of recombinant protein G agarose beads were added and incubated overnight at 4° C. on a shaking platform. The beads were pelletized (2 min., 2.400 rpm, 4° C.) and washed twice with 500 µl ice-cold PBS. After the dried agarose beads were topped up with 30 µl Laemmli buffer and incubated at 95° C. for 5 min. 20 ul were loaded on a 10% SDS-PAGE (sodium dodecyl sulfate polyacrylamide gel electrophoresis) and run at 125V. After the gel was blotted on a nitrocellulose blotting membrane (0.45 µm), the membrane was blocked with 10% BSA/TBS-T (0.1% Tween20) for one hour at room temperature on a shaking platform. Afterwards the membrane was incubated with the primary antibody (anti-STAT3 1:1.000 in TBS-T) overnight at 4° C. on a shaking platform. After three washing steps (15 min., 10 min., 10 min. with TBS-T) with TBS-T the membrane were incubated with ECLTM Anti-Rabbit IgG, horseradish peroxidase (1:10.000 in TBS-T) at 4° C. on a shaking platform for 2-4 hours. The detection took place using the SuperSignal® West Dura Extended detection kit after four final washing steps (5 min. ea. with TBS-T).

Figure 6:
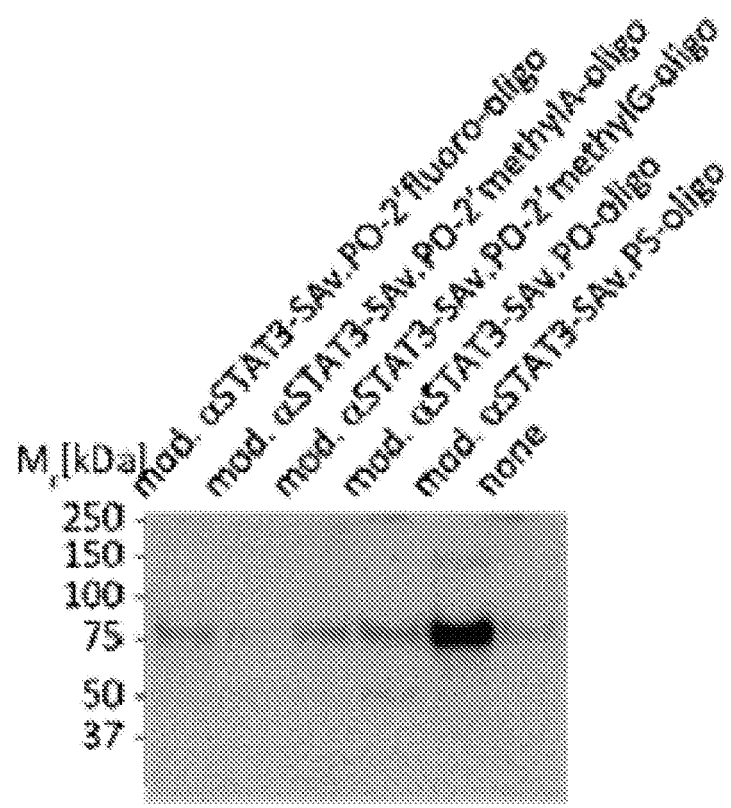
FIG. 6: Modified anti-STAT3 antibodies conjugated to PS-DNA oligos via Streptavidin/Biotin are capable of cell-penetration and target recognition.

Modified anti-STAT3 antibodies conjugated to PS-DNA oligos via Streptavidin/Biotin are capable of cell-penetration and target recognition. FIG. 6 shows alternative Western blotting analysis to detect delivered antibody-antigen complex. U251 cells treated with modified anti-STAT3 antibodies conjugated to PO-2'fluoro-oligo (first lane), PO-2'methylA-oligo (second lane), PO-2'methylG-oligo (third lane), PO-oligo DNA (20mer) (fourth lane), PS-oligo DNA (20mer) (fifth lane) and none modified antibody (sixth lane) via Streptavidin/Biotin. The U251 cells were treated with 10 µl g/ml of the indicated modified anti-STAT3 antibodies and were incubated for one hour at 37° C. After the incubation and two washing steps with PBS (2 ml) the cells were lysed via incubation (30 min.) on ice in 500 µl RIPA buffer, followed by vigorous vortexing. The full cell lysates were harvested by collecting the supernatant after a centrifugation step (10 min. 13.000 rpm, 4° C.). To each full cell lysate 30 µl of recombinant protein G agarose beads were added and incubated overnight at 4° C. on a shaking platform. The beads were pelletized (2 min., 2.400 rpm, 4° C.) and washed twice with 500 µl ice-cold PBS. After the dried agarose beads were topped up with 30 µl Laemmli buffer and incubated at 95° C. for 5 min. 20 ul were loaded on a 10% SDS-PAGE (sodium dodecyl sulfate polyacrylamide gel electrophoresis) and run at 125V. After the gel was blotted on a nitrocellulose blotting membrane (0.45 µm), the membrane was blocked with 10% BSA/TBS-T (0.1% Tween20) for one hour at room temperature on a shaking platform. Afterwards the membrane was incubated with the primary antibody (anti-STAT3 1:1.000 in TBS-T) overnight at 4° C. on a shaking platform. After three washing steps (15 min., 10 min., 10 min. with TBS-T) with TBS-T the membrane were incubated with ECLTM Anti-Rabbit IgG, horseradish peroxidase (1:10.000 in TBS-T) at 4° C. on a shaking platform for 2-4 hours. The detection took place using the SuperSignal® West Dura Extended detection kit after four final washing steps (5 min. ea. With TBS-T).

Figure 7A:
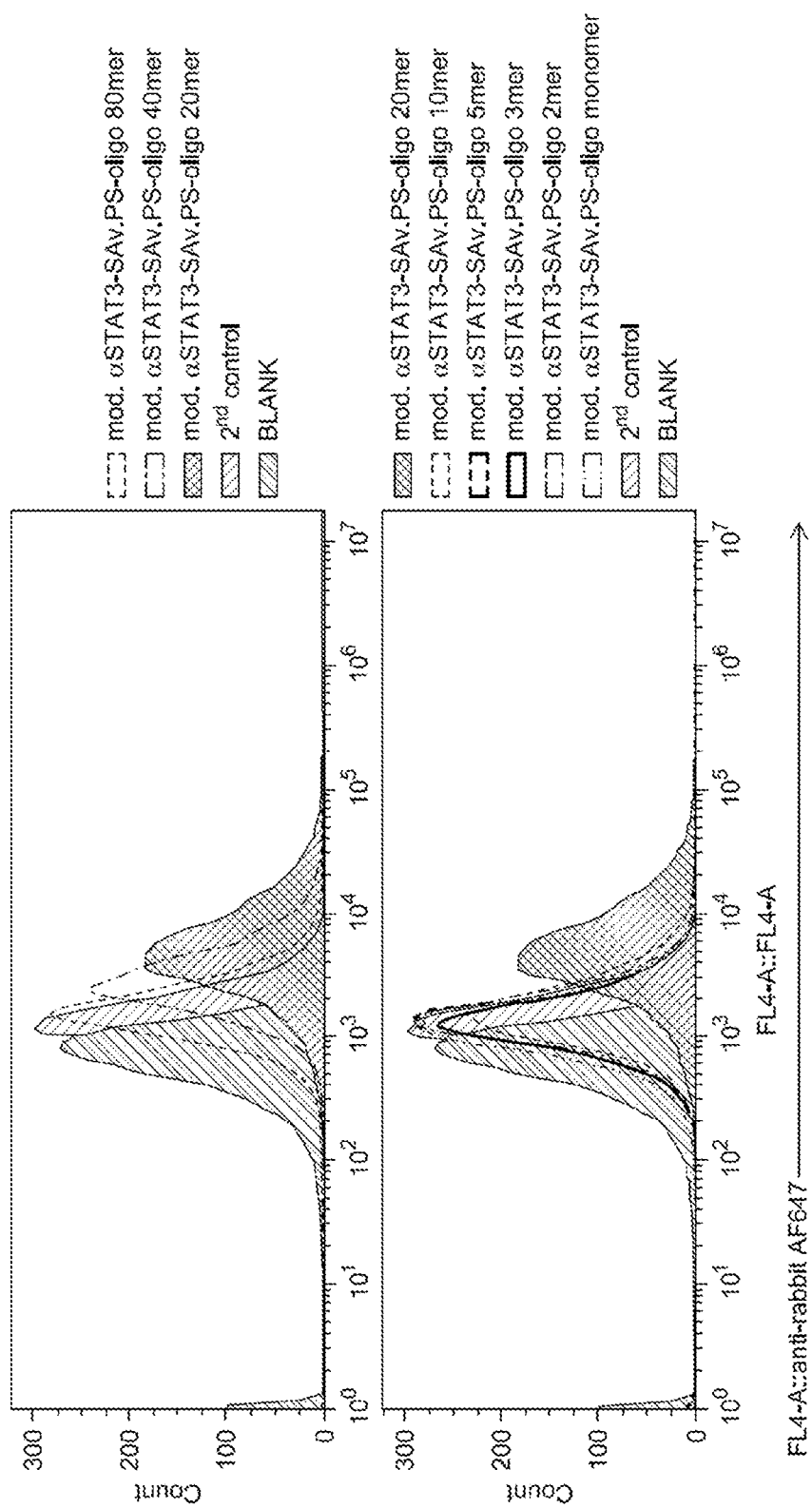
FIG. 7A and FIG. 7B: Modified anti-STAT3 antibodies conjugated to PS-DNA oligo (20 mer) via Streptavidin/Biotin are most efficient in cell-penetration

Modified anti-STAT3 antibodies conjugated to PS-DNA oligo (20 mer) via Streptavidin/Biotin are most efficient in cell-penetration. FIG. 7A upper panel shows flow cytometry analysis to detect delivered antibodies, using an anti-rabbit antibody. U251 cells (human glioma stem cells) were treated with modified anti-STAT3 antibodies (rabbit) conjugated to indicated PS DNA-oligos: (80mer) (pointed line), PS-oligo DNA (40mer) (dashed line) and PS-oligo DNA (20mer) (red area) via Streptavidin/Biotin. FIG. 7A lower panel shows same as FIG. 7A, but the U251 cells were treated with modified anti-STAT3 antibodies conjugated to PS-oligo DNA (20mer) (red area), PS-oligo DNA (10mer) (blue line), PS-oligo DNA (5mer) (red line) PS-oligo DNA (3mer) (orange line), PS-oligo DNA (2mer) (light green line) and PS-oligo DNA (monomer) (dark green line) via Streptavidin/Biotin. The U251 cells were treated with 10 µg/ml of the indicated modified anti-STAT3 antibody (rabbit) and were incubated for one hour at 37° C. After a washing step (PBS/1% BSA), the cells were harvested and fixed with 500 µl 2% paraformaldehyde (15 min.) followed by a washing step (PBS/1% BSA) and proceeded by 500 ice-cold methanol (10 min.). After washing (PBS/1% BSA) the cells were blocked with PBS/1% BSA/1% mouse serum for one hour at 4° C. Afterwards the cells were washed (PBS/1% BSA) and stained with a secondary antibody (grey line, upper and lower panel) (αRb AF647 1:4.000 in PBS) for 30 min. in the dark. The flow analysis was performed after three final washing steps (PBS/1% BSA) and collecting the cells in 300 µl of washing buffer. Unstained U251 were used as a blank control (grey area, upper and lower panel).

Figure 7B:
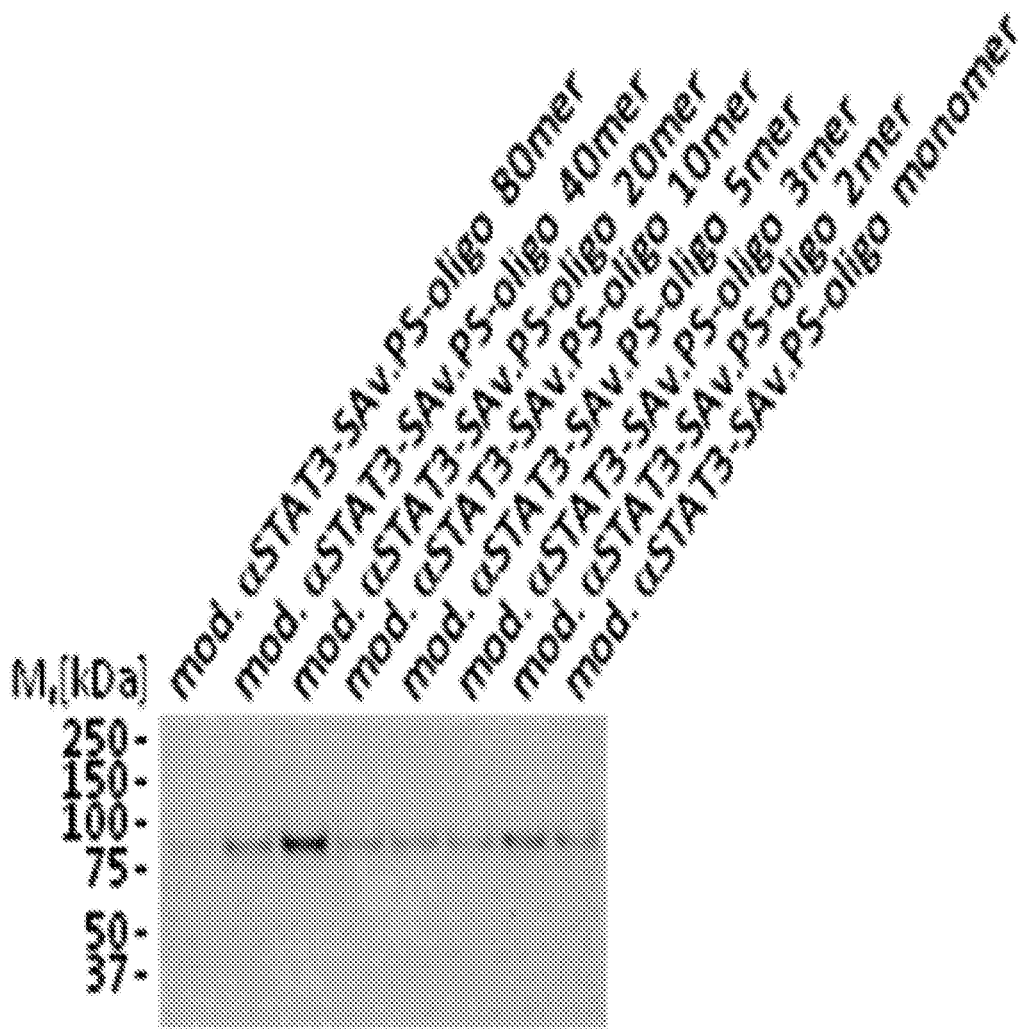

FIG. 7B shows alternative Western blotting analysis to detect delivered antibody-antigen complex. U251 cells were treated with modified anti-STAT3 antibodies conjugated to PS-DNA oligo DNA (80mer) (first lane), PS-oligo DNA (40mer) (second lane), PS-oligo DNA (20mer) (third lane), PS-oligo DNA (10mer) (fourth lane), PS-oligo DNA (5mer) (fifth lane), PS-oligo DNA (3mer) (sixth lane), PS-oligo DNA (2mer) (seventh lane) and PS-oligo DNA (monomer) (eight lane) via Streptavidin/Biotin. The U251 cells were treated with 10 µg/ml of indicated modified anti-STAT3 antibodies and were incubated for one hour at 37° C. After the incubation and two washing steps with PBS (2 ml) the cells were lysed via incubation (30 min.) on ice in 500 µl RIPA buffer, followed by vigorous vortexing. The full cell lysates were harvested by collecting the supernatant after a centrifugation step (10 min. 13.000 rpm, 4° C.). To each full cell lysate 30 µl of recombinant protein G agarose beads were added and incubated overnight at 4° C. on a shaking platform. The beads were pelletized (2 min., 2.400 rpm, 4°

C.) and washed twice with 500 µl ice-cold PBS. After the dried agarose beads were topped up with 30 µl Laemmli buffer and incubated at 95° C. for 5 min. 20 ul were loaded on a 10% SDS-PAGE (sodium dodecyl sulfate polyacrylamide gel electrophoresis) and run at 125V. After the gel was blotted on a nitrocellulose blotting membrane (0.45 µm), the membrane was blocked with 10% BSA/TBS-T (0.1% Tween20) for one hour at room temperature on a shaking platform. Afterwards the membrane was incubated with the primary antibody (anti-STAT3 1:1.000 in TBS-T) overnight at 4° C. on a shaking platform. After three washing steps (15 min., 10 min., 10 min. with TBS-T) with TBS-T the membrane were incubated with ECLTM Anti-Rabbit IgG, horseradish peroxidase (1:10.000 in TBS-T) at 4° C. on a shaking platform for 2-4 hours. The detection took place using the SuperSignal® West Dura Extended detection kit after four final washing steps (5 min. each with TBS-T).

Figure 8A:
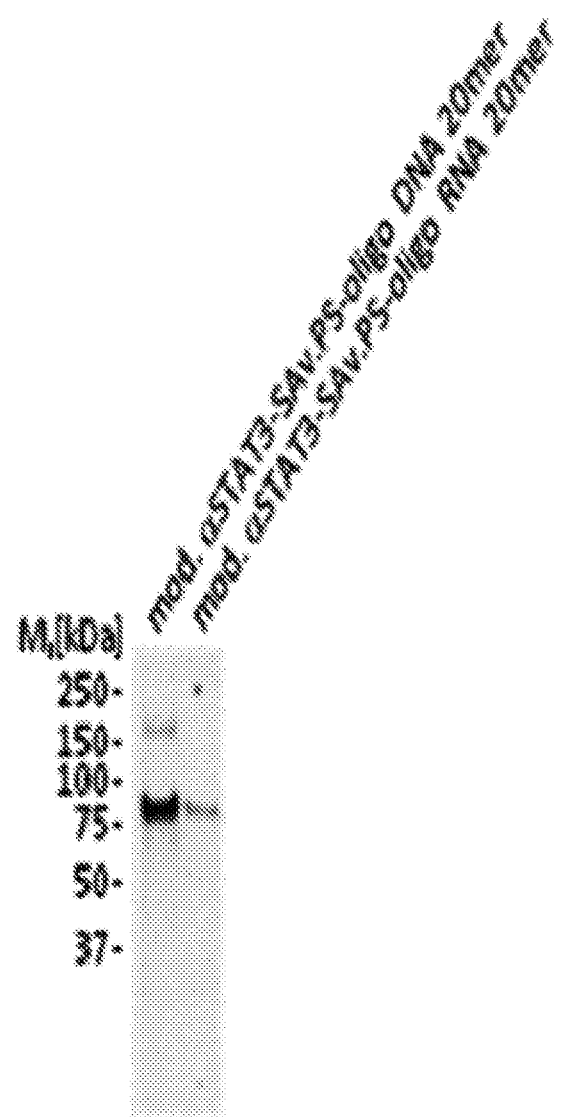
FIG. 8A and FIG. 8B: Modified anti-STAT3 antibodies conjugated to PS-DNA oligo (20mer) via Streptavidin/Biotin are capable of cell-penetration.

Modified anti-STAT3 antibodies conjugated to PS-DNA oligo (20mer) via Streptavidin/Biotin are capable of cell-penetration. FIG. 8A: Alternative Western blotting analysis of U251 cells treated with modified anti-STAT3 antibodies conjugated to PS-oligo DNA (20mer) (first lane) and PS-oligo RNA (20mer) (second lane) via Streptavidin/Biotin. The U251 cells were treated with 10 µg/ml of indicated modified anti-STAT3 antibodies and were incubated for one hour at 37° C. After the incubation and two washing steps with PBS (2 ml) the cells were lysed via incubation (30 min.) on ice in 500 µl RIPA buffer, followed by vigorous vortexing. The full cell lysates were harvested by collecting the supernatant after a centrifugation step (10 min. 13.000 rpm, 4° C.). To each full cell lysate 30 µl of recombinant protein G agarose beads were added and incubated overnight at 4° C. on a shaking platform. The beads were pelletized (2 min., 2.400 rpm, 4° C.) and washed twice with 500 µl ice-cold PBS. After the dried agarose beads were topped up with 30 µl Laemmli buffer and incubated at 95° C. for 5 min. 20 ul were loaded on a 10% SDS-PAGE (sodium dodecyl sulfate polyacrylamide gel electrophoresis) and run at 125V. After the gel was blotted on a nitrocellulose blotting membrane (0.45 µm), the membrane was blocked with 10% BSA/TBS-T (0.1% Tween20) for one hour at room temperature on a shaking platform. Afterwards the membrane was incubated with the primary antibody (anti-STAT3 1:1.000 in TBS-T) overnight at 4° C. on a shaking platform. After three washing steps (15 min., 10 min., 10 min. with TBS-T) with TBS-T the membrane were incubated with ECLTM Anti-Rabbit IgG, horseradish peroxidase (1:10.000 in TBS-T) at 4° C. on a shaking platform for 2-4 hours. The detection took place using the SuperSignal® West Dura Extended detection kit after four final washing steps (5 min. ea. With TBS-T).

Figure 8B:
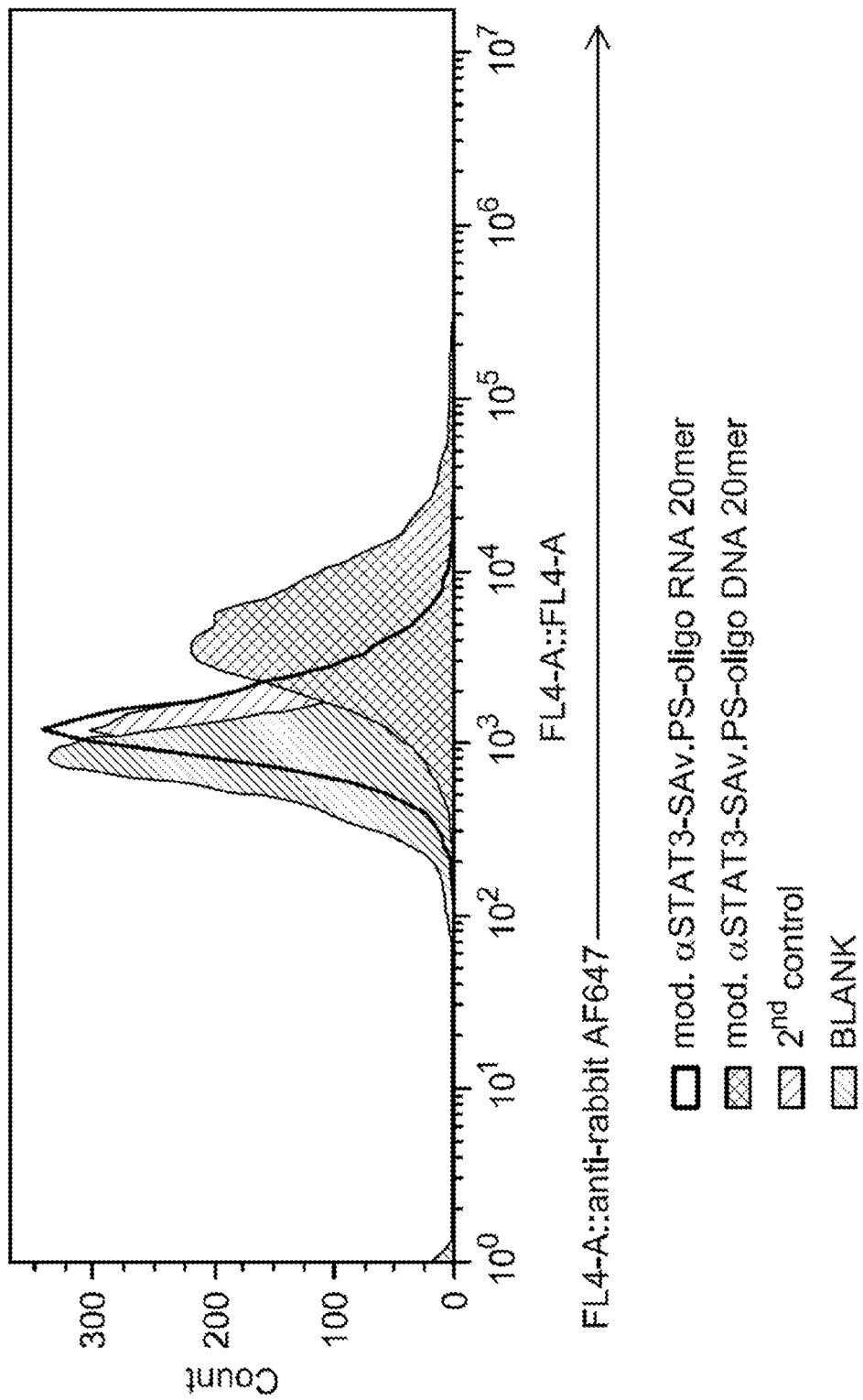

FIG. 8B: Flow cytometry analysis of U251 cells (human glioma stem cells) treated with modified anti-STAT3 antibodies conjugated to PS-RNA oligo (20mer) (black line) and PS-DNA oligo (20mer) (red area) via Streptavidin/Biotin. The U251 cells were treated with 10 µg/ml of the indicated modified anti-STAT3 antibodies and were incubated for one hour at 37° C. After a washing step (PBS/1% BSA), the cells were harvested and fixed with 500 µl 2% paraformaldehyde (15 min.) followed by a washing step (PBS/1% BSA) and proceeded by 500 ice-cold methanol (10 min.). After washing (PBS/1% BSA) the cells were blocked with PBS/1% BSA/1% mouse serum for one hour at 4° C. Afterwards the cells were washed (PBS/1% BSA) and stained with a secondary antibody (grey line) (αRb AF647 1:4.000 in PBS) for 30 min. in the dark. The flow analysis was performed after three final washing steps (PBS/1% BSA) and collecting the cells in 300 µl of washing buffer. Unstained U251 were used as a blank control (grey area).

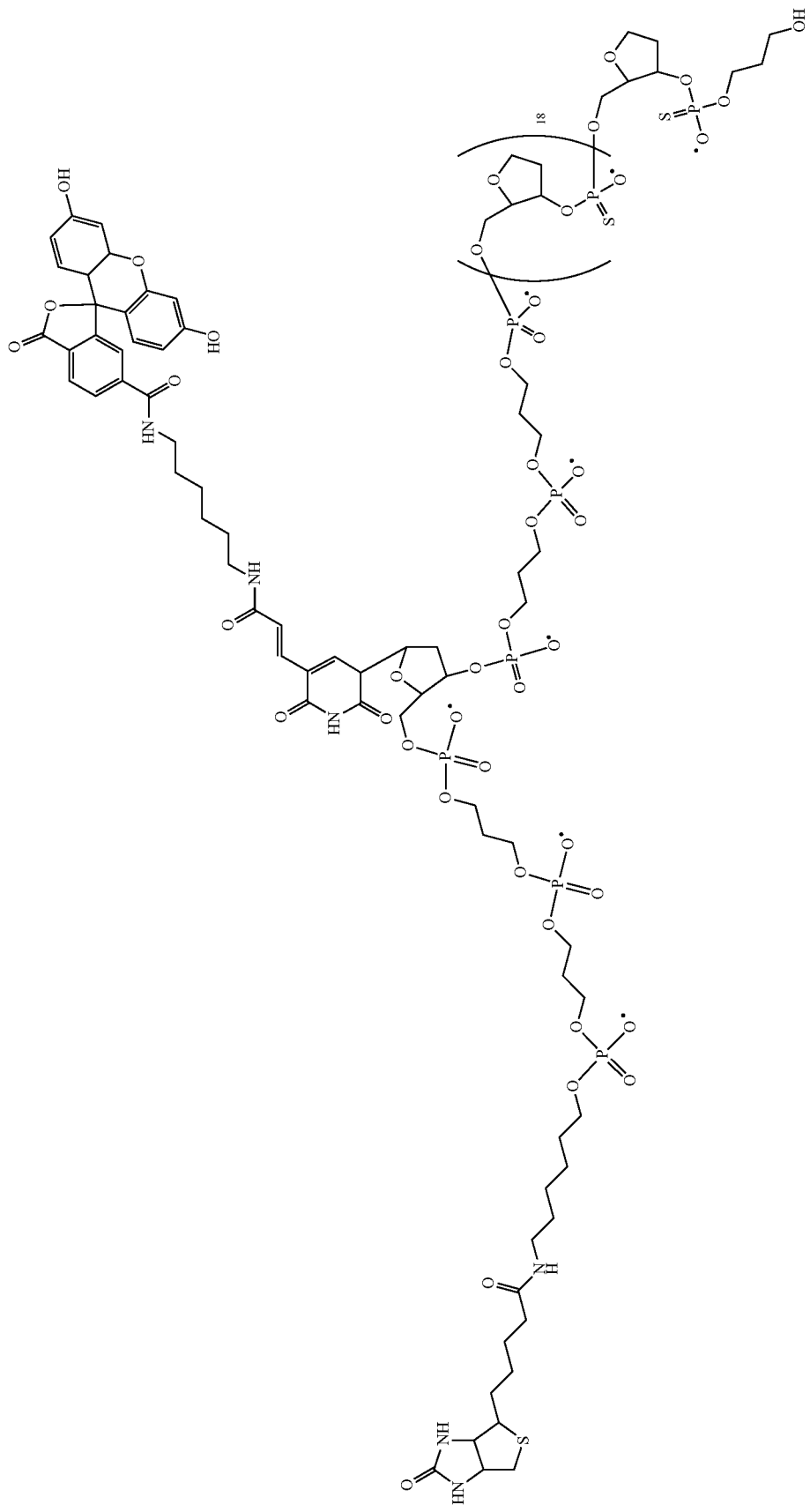
Structures of 5'-biotin abasic oligo
PS linkage between dR:

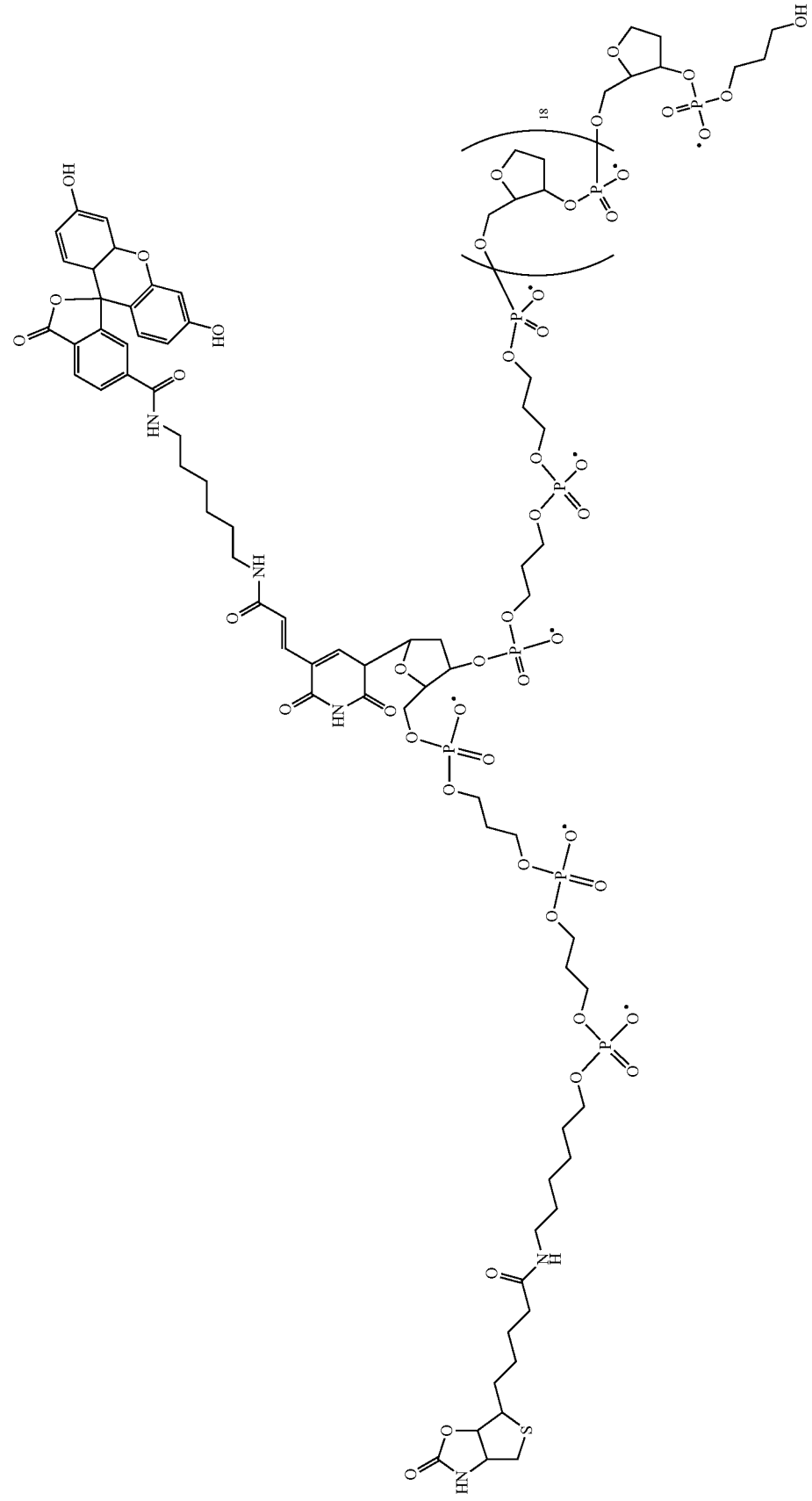

Figure 9A:
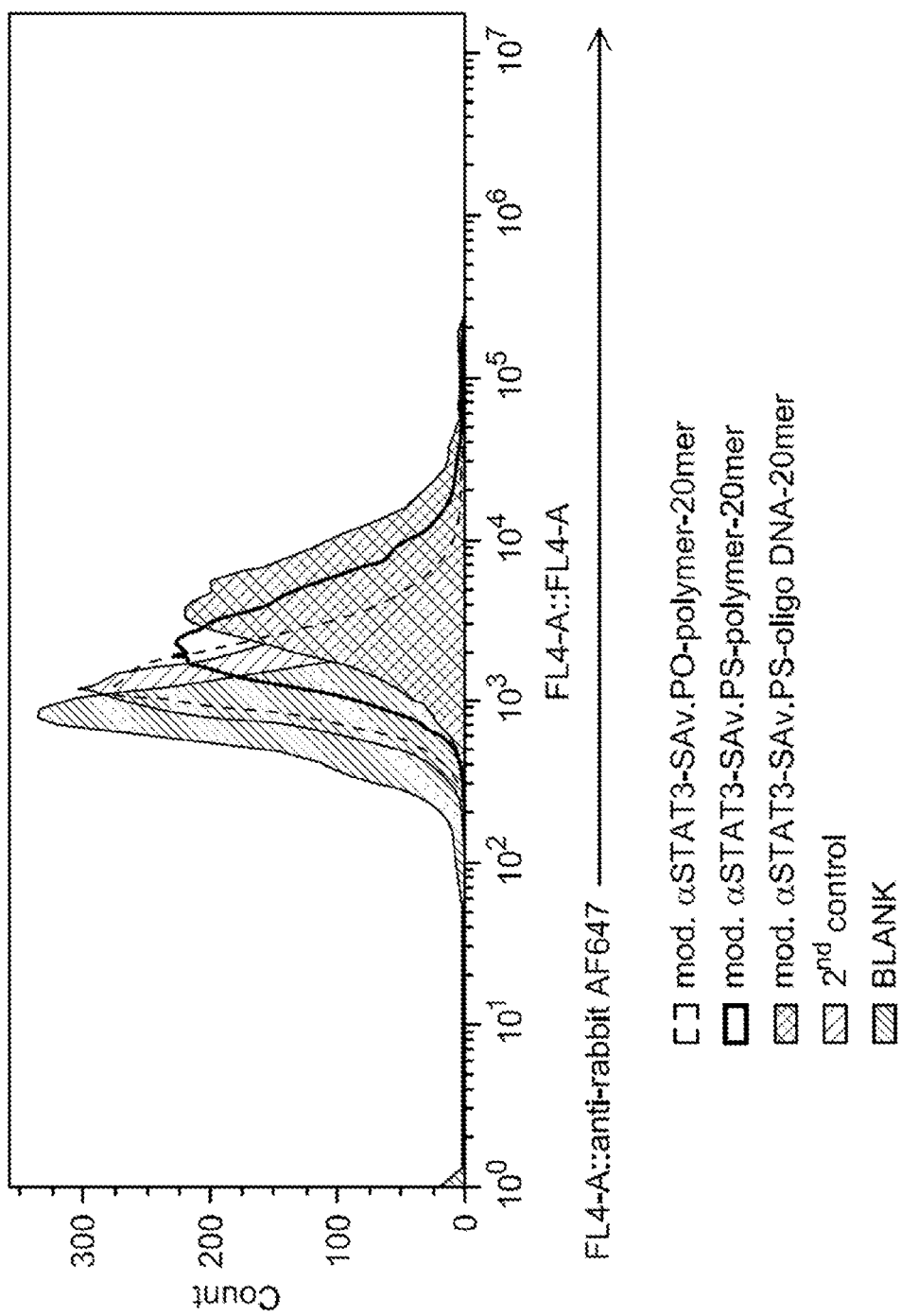
FIG. 9A and FIG. 9B: Modified anti-STAT3 antibodies conjugated to PS-DNA oligo (20mer) via Streptavidin/Biotin are capable of cell-penetration.
Figure 9B:
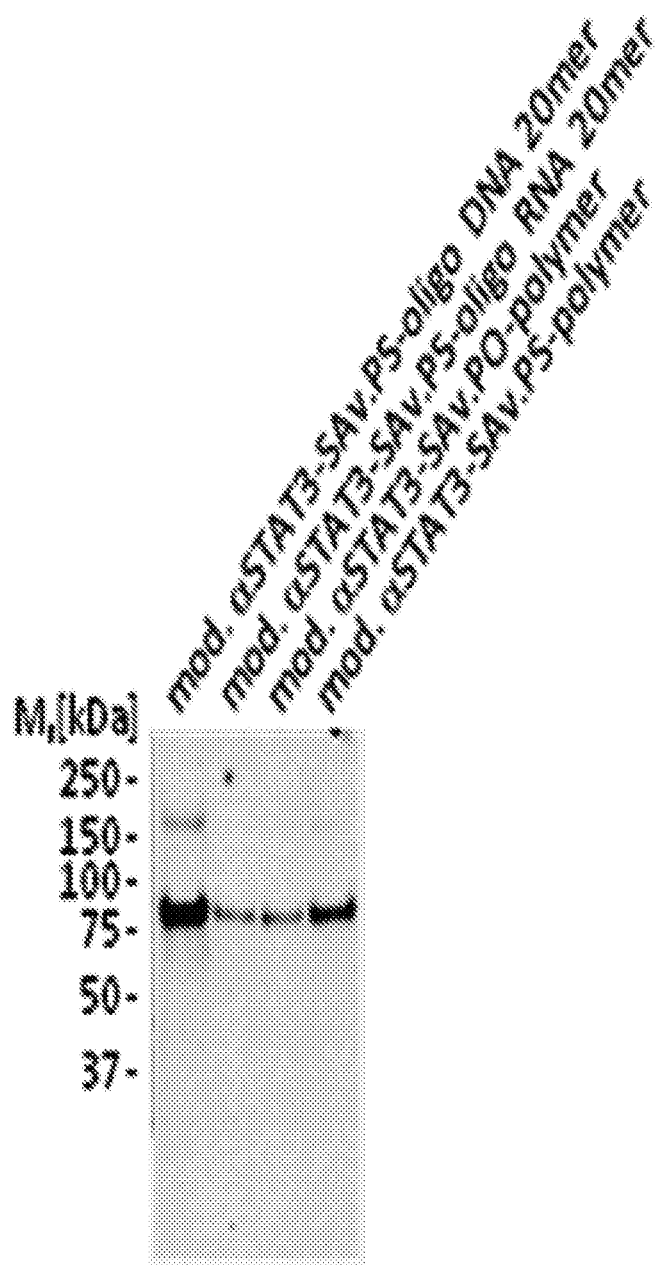

FIG. 9A depicts flow cytometry analysis of U251 cells (human glioma stem cells) treated with modified anti-STAT3 antibodies conjugated to PO-polymer (20mer) (dashed line), PS-polymer (20mer) (black line), PS-oligo DNA (20mer) (red area) via Strepavidin/Biotin. The U251 cells were treated with 10 µg/ml of the particular modified anti-STAT3 antibody and were incubated for one hour at 37° C. After a washing step (PBS/1% BSA), the cells were harvested and fixed with 500 µl 2% paraformaldehyde (15 min.) followed by a washing step (PBS/1% BSA) and proceeded by 500 ice-cold methanol (10 min.). After washing (PBS/1% BSA) the cells were blocked with PBS/1% BSA/1% mouse serum for one hour at 4° C. Afterwards the cells were washed (PBS/1% BSA) and stained with a secondary antibody (grey line) (αRb AF647 1:4.000 in PBS) for 30 min. in the dark. The flow analysis was performed after three final washing steps (PBS/1% BSA) and collecting the cells in 300 µl of washing buffer. Unstained U251 were used as a blank control (grey area).

FIG. 9A depicts alternative Western blotting analysis of U251 cells treated with modified anti-STAT3 antibodies conjugated to PS-oligo DNA (20mer) (first lane), PS-oligo RNA (20mer) (second lane), PO-polymer (20mer) (third lane) and PS-polymer (20mer) (fourth lane) via Strepavidin/Biotin. The U251 cells were treated with 10 µg/ml of the particular modified anti-STAT3 antibody and were incubated for one hour at 37° C. After the incubation the cells were lysed via incubation (30 min.) on ice in 500 µl RIPA buffer, followed by vigorous vortexing. The full cell lysates were harvested by collecting the supernatant after a centrifugation step (10 min. 13.000 rpm, 4° C.). To each full cell lysate 30 µl of recombinant protein G agarose beads were added and incubated overnight at 4° C. on a shaking platform. The beads were pelletized (2 min., 2.400 rpm, 4° C.) and washed twice with 500 µl ice-cold PBS. After the dried agarose beads were topped up with 30 µl laemmli buffer and incubated at 95° C. for 5 min. 20 ul were loaded on a 10% SDS-PAGE (sodium dodecyl sulfate polyacrylamide gel electrophoresis) and run at 125V. After the gel was blotted on a nitrocellulose blotting membrane (0.45 µm), the membrane was blocked with 10% BSA/TBS-T (0.1% Tween20) for one hour at room temperature on a shaking platform. Afterwards the membrane was incubated with the primary antibody (anti-STAT3 1:1.000 in TBS-T) overnight at 4° C. on a shaking platform. After three washing steps (15 min., 10 min., 10 min. with TBS-T) with TBS-T the membrane were incubated with ECLTM Anti-Rabbit IgG, horseradish peroxidase (1:10.000 in TBS-T) at 4° C. on a shaking platform for 2-4 hours. The detection took place using to SuperSignal® West Dura Extended detection kit after four final washing steps (5 min. ea. With TBS-T).

Example 2

Modulating Th1 Immunity Through Anti-T-Bet Cell-Penetrating Antibody

T-bet (T-box transcription factor TBX21(TBX21)) is a transcription factor critical for Th1 differentiation. Inhibitors of T-Bet can treat type 2 diabetes, obesity and other inflammatory diseases. In contrast, stimulating T-bet can activate anti-tumor and anti-viral immunity. However, there are no T-bet modulators. Here Applicants show a particular T-bet antibody, when modified (non-covalently linked to phosphorothioated (PS) DNA oligomers at a 20mer through avidin/streptavidin), serves as an effective T-bet agonist, stimulates Th1 immune responses, recruits CD8+ T cells to tumors through stimulating dendritic cells, and inhibits tumor growth.

Cell-Penetrating T-Bet Antibody Treatment Restricts Mouse Melanoma Development

Figure 10:
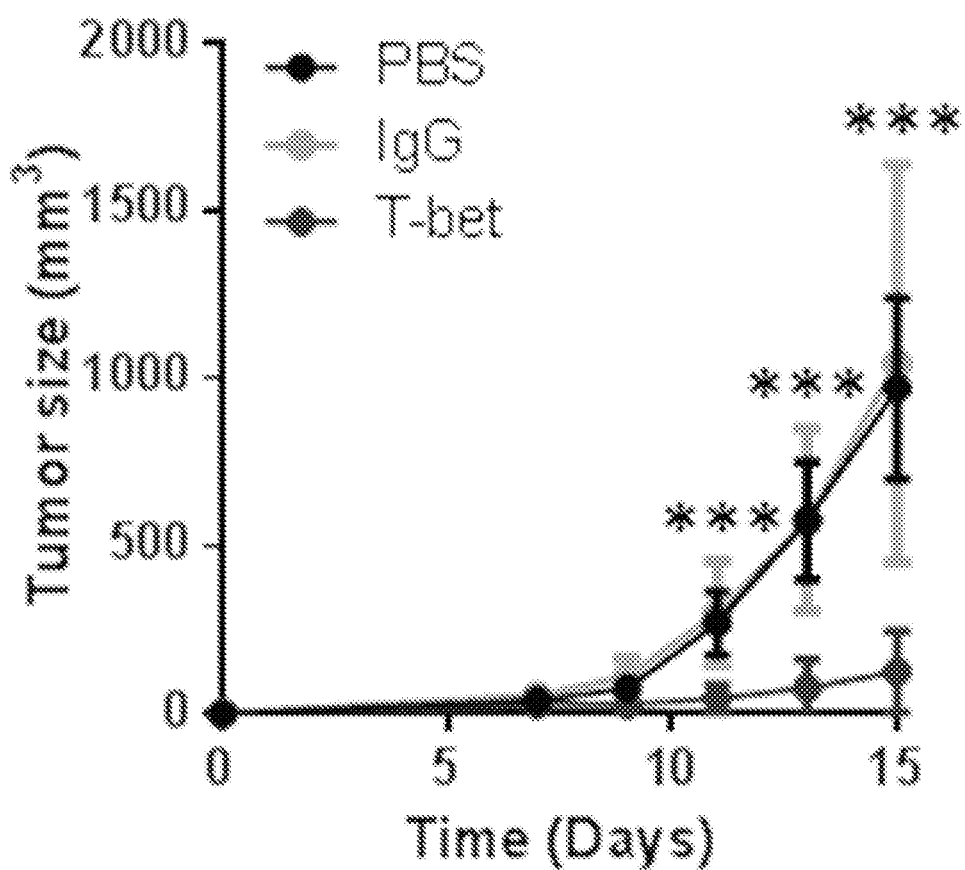
FIG. 10: Tumor growth of mouse B16 melanoma upon treatment with modified anti-T-Bet antibody. 1×105 B16 tumor cells were injected subcutaneously on day 0 in C57/BL6 mice, followed by local administrations of vehicle (PBS), modified control (IgG) and T-bet antibodies (10 ug/dose) starting from day 7. Antibody treatments were given every other day. SD shown; T-test: ***) P<0.001.

To test the therapeutic efficacy of modified cell-penetrating T-Bet antibody, B16 mouse melanoma tumors were treated locally with 10 µg/dose every other day and tumor growth was monitored. Comparing to PBS treated (vehicle control) or modified non-targeting IgG treated groups, administration of modified anti-T-Bet antibody resulted in significant tumor growth restriction (FIG. 10).

Modified T-Bet Antibody Activates Anti-Tumor Adaptive Immune Responses

Figure 11:
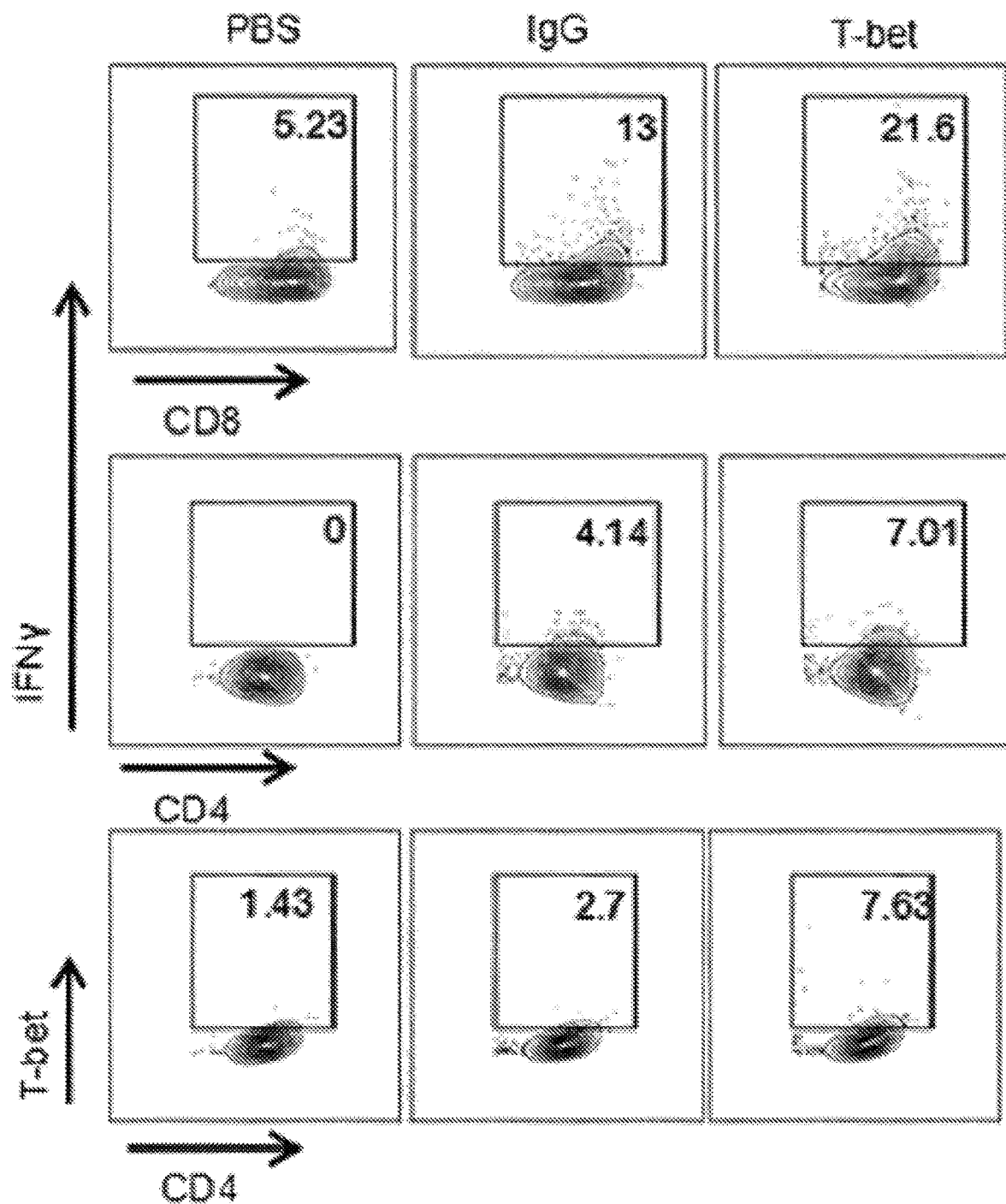
FIG. 11: Modified T-Bet antibody enhanced IFNγ-expressing CD4+ and CD8+ T cells in tumors. B16 tumor associated lymphocytes were analyzed by flow cytometry for CTL maturation and Th1 population as well as T-bet expression by CD4+ T cells.

T-Bet is known to be expressed in different types of immune cells, especially T cell, B cells and Dendritic cells (DCs). Tumor infiltrating lymphocytes were isolated from B16 mouse melanoma treated as mentioned in FIG. 10 legend, and subjected to flow cytometry analysis. Treatment of T-Bet antibody significantly enhanced Th1 immune response as well as functional cytotoxic T lymphocytes (an increased in IFNγ-expressing $CD4^+$ and $CD8^+$ T cells). In addition, in vivo treatment of T-Bet antibody promoted T-Bet expression in $CD4^+$ T cells, indicating it served as a T-bet agonist to stimulate Th1 immune responses (FIG. 11).

Figure 12A:
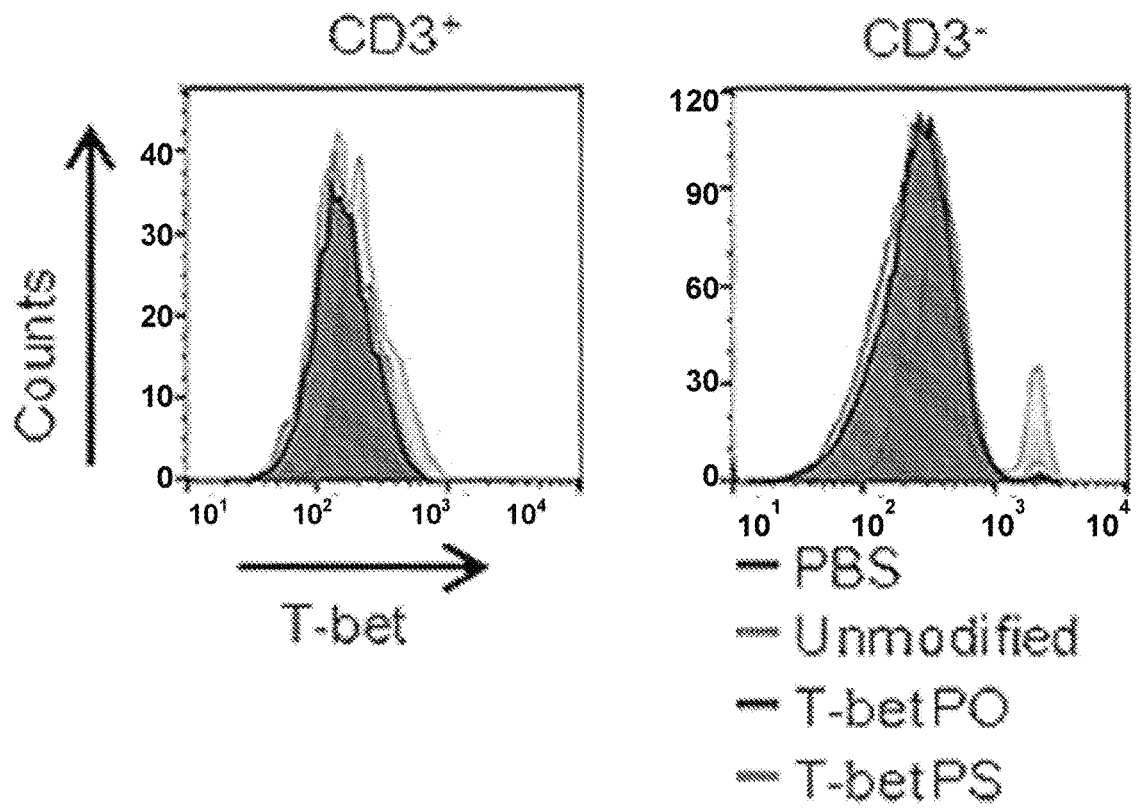
FIG. 12A and FIG. 12B: T-Bet antibody promotes DC function at tumor sites. Flow cytometry analysis of T-Bet antibody uptake in CD3+ or CD3- tumor associated lymphocytes with PBS, Unmodified T-Bet, PO or PS modified T-Bet antibody treatment, (FIG. 12A), and CD86, MHC II expression in CD11c+ DCs in these groups, (FIG. 12B).
Figure 12B:
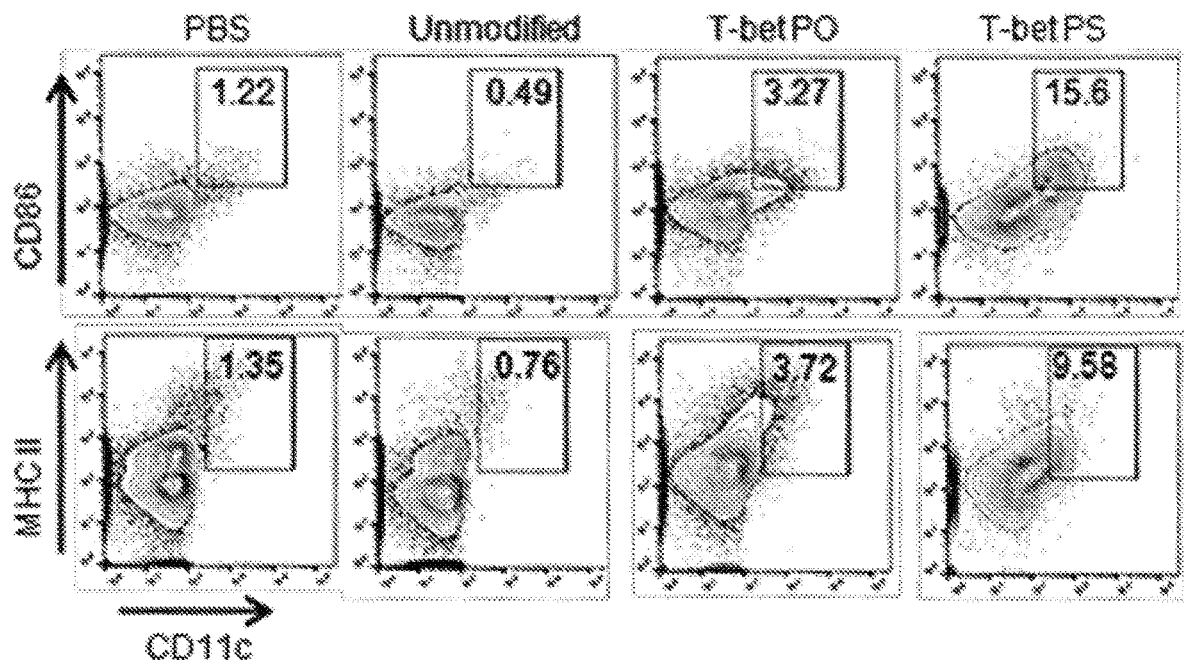

Cell-Penetrating T-Bet Antibody Also Targets DCs and Enhances their Antigen-Presenting Function Detailed analysis of T-Bet antibody uptake in different immune cells unveiled that the antibody was also uptaken by $CD3^-$ cells, which Applicants further identified as $CD11c^+$ DCs (data not shown). Treatment of modified T-Bet antibody was able to promote antigen-presentation function of DCs, through expressing of CD86 and MHC II (FIG. 12A and FIG. 12B).

Example 3

Blocking FoxP3 with Cell-Penetrating Antibody Suppresses Tumor Tregs and Tumor Progression Tregs (regulatory T cells) inhibit anti-tumor/viral immune responses, thereby impeding various immunotherapies. It is of great importance to develop novel immunotherapeutics to reduce Tregs. FoxP3 is essential for Treg's maintenance and function. However, FoxP3 is deemed undruggable due to its intracellular distribution. Here Applicants show that PS-modified FoxP3 antibody is able to preferentially target FoxP3-positive cells, inhibits levels of FoxP3 and downstream effector, CTLA4. More importantly, systemic administration of modified FoxP3 antibody could reduce tumor-infiltrating Tregs and tumor growth.

Cell-Penetrating FoxP3 Antibody is Preferentially Retained by Tregs

Figure 13:
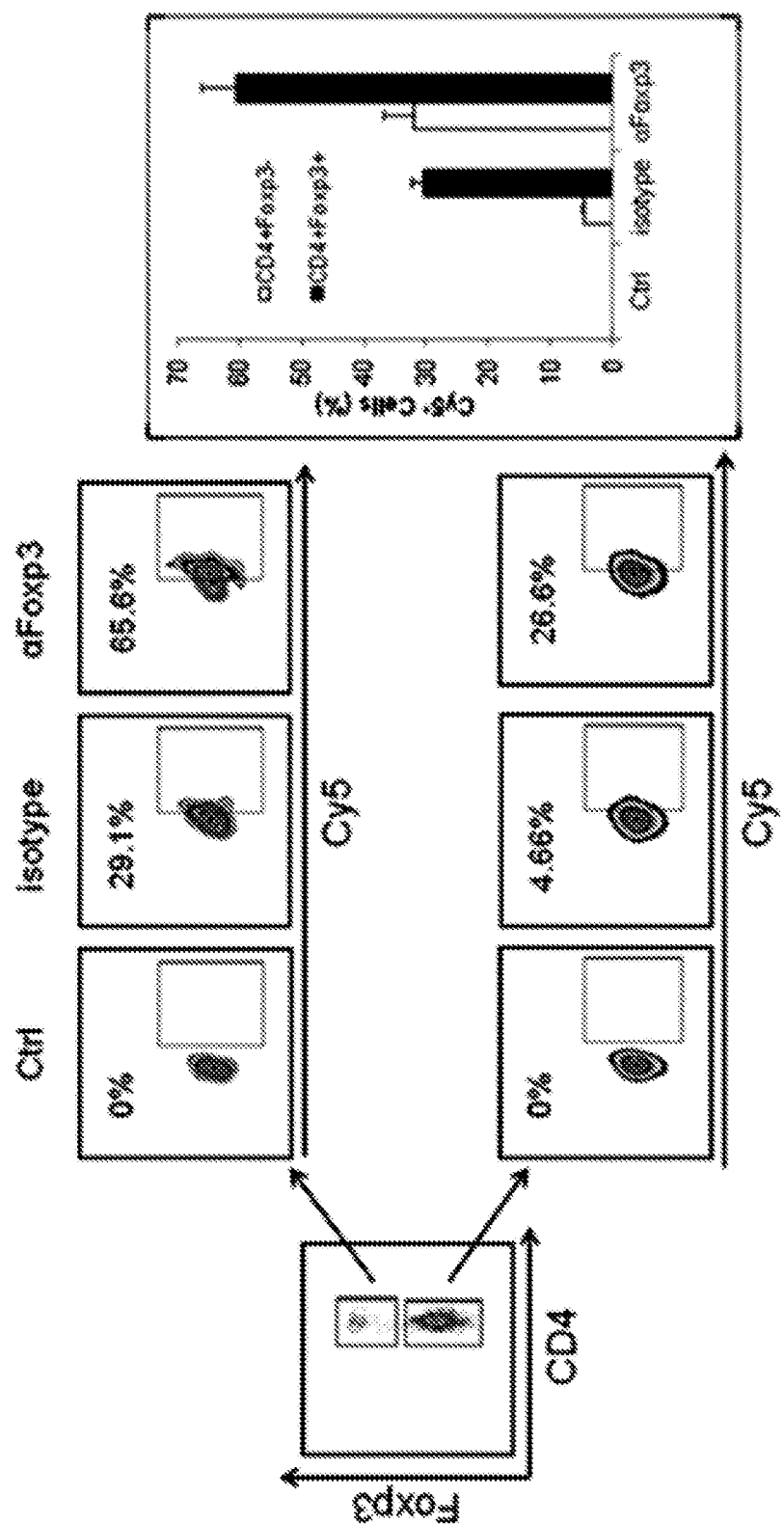
FIG. 13: Specificity of the cell-penetrating FoxP3 antibodies. 10 μg/ml modified antibodies (isotype or αFoxp3) were cultured with splenocytes ($2 \times 10^6$/ml) freshly isolated from Foxp3-GFP transgenic mice for 2 hours, and all cells are collected and subjected to flow cytometry analysis.

To assess the specificity of the modified cell-penetrating FoxP3 antibody, freshly isolated splenocytes from FoxP3-GFP-Tg mice were cultured with 10 µg/ml modified FoxP3 antibody or with 10 µg/ml modified IgG, which serves as control. 2 hours later cells were collected, washed and subjected to flow cytometry analysis for detection of Cy5, which was used to label PS oligo conjugated to the antibodies. Notably, FoxP3+ Tregs could retain much more the modified FoxP3 antibodies than non-Tregs. And FoxP3 antibody was more detectable in Tregs much more than the control modified IgG groups (FIG. 13).

Figure 14:
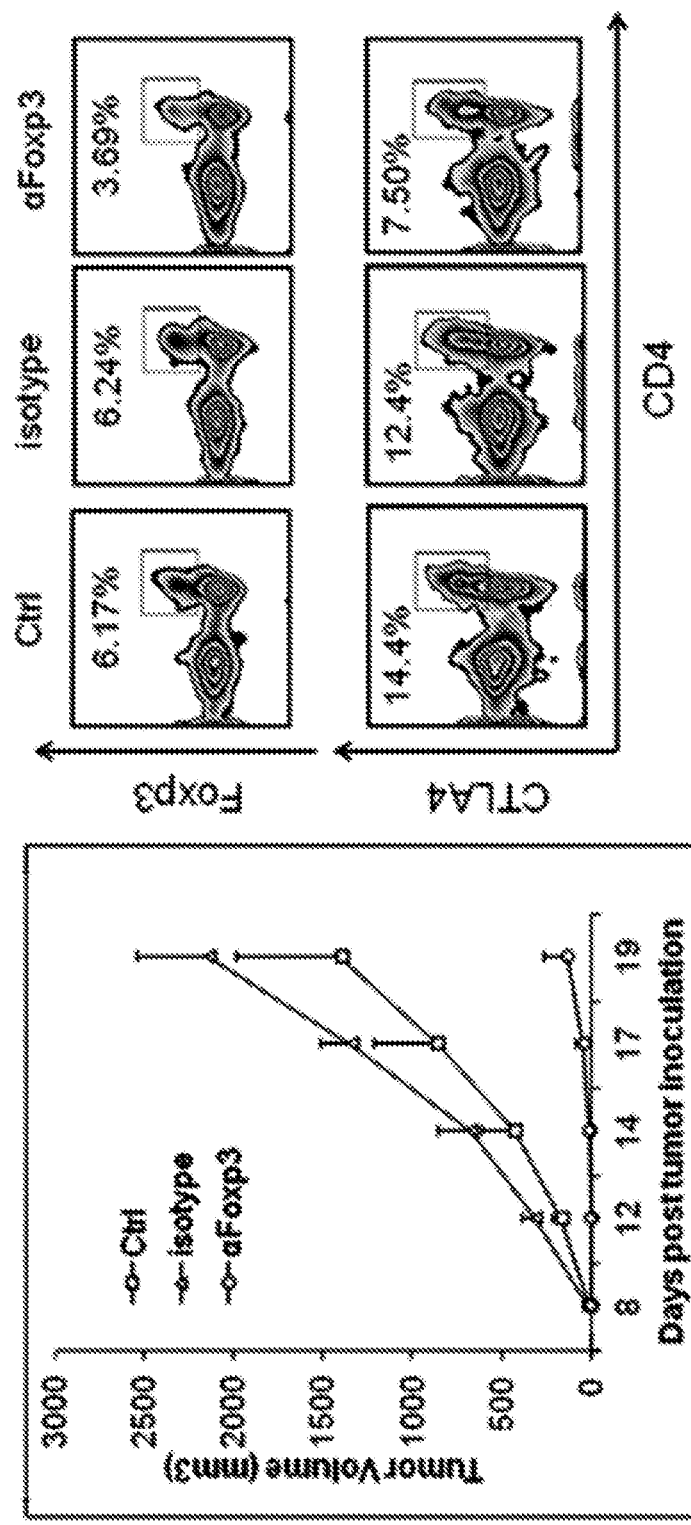
FIG. 14: Targeting FoxP3 by the cell-penetrating antibody reduces tumor-associated Tregs and tumor growth. 0.2 million B16 tumor cells were injected s.c., followed by i.v. administration of modified control (IgG) and Foxp3 antibodies (10 ug/mouse) one day after. Four more antibody treatments were given systemically every other day until day 11 (note: no more treatments after day 11). At day 20 all animals were euthanized and tumor lymphocytes were isolated through gradient centrifugation. Then tumor infiltrating lymphocytes were fixed and permeabilized for intracellular staining of FoxP3 and CTLA4.

Systemic Treatments with Modified FoxP3 Antibody Decrease FoxP3-Positive and CTLA4-Positive CD4+ T Cells (Tregs) and Abrogates Melanoma Growth To examine the effect of modified FoxP3 on T cells, modified IgG or FoxP3 antibodies (10 µg/mouse) were administrated systemically to C57BL/6 mice, right after B16 tumor cell inoculation, every other day for until day 11. Tumor volume was monitored every one or two days and all animals were euthanized after 19 days. Tumors were then collected and tumor infiltrating lymphocytes were isolated for further flow cytometric analysis to detect FoxP3 and CTLA4 positive T cells. Compared to modified non-targeting IgG, systemic administration of the modified anti-FoxP3 antibody significantly reduced melanoma progression. Further analysis of tumor-infiltrating lymphocytes showed that the percentages of FoxP-positive and CTLA4-positive CD4+ T cells were decreased, indicating blockage of tumor Tregs by the modified FoxP3 antibodies (FIG. 14).

EMBODIMENTS

Embodiment 1

A cell-penetrating conjugate comprising:
(i) a non-cell penetrating protein;
(ii) a phosphorothioate nucleic acid; and
(iii) a non-covalent linker attaching said phosphorothioate nucleic acid to said non-cell penetrating protein, said non-covalent linker comprising a biotin-binding domain non-covalently attached to a biotin domain; and wherein said phosphorothioate nucleic acid enhances intracellular delivery of said non-cell penetrating protein.

Embodiment 2

The cell-penetrating conjugate of embodiment 1, wherein said biotin-binding domain is an avidin domain.

Embodiment 3

The cell-penetrating conjugate of embodiment 1, wherein said biotin-binding domain is a streptavidin domain.

Embodiment 4

The cell-penetrating conjugate of embodiment 3, wherein said streptavidin domain binds a plurality of biotin domains.

Embodiment 5

The cell-penetrating conjugate of embodiment 4, wherein said streptavidin domain binds about four biotin domains.

Embodiment 6

The cell-penetrating conjugate of any one of embodiments 1-5, wherein said biotin-binding domain is covalently attached to said non-cell penetrating protein.

Embodiment 7

The cell-penetrating conjugate of any one of embodiments 1-6, wherein a plurality of biotin-binding domains are attached to said non-cell penetrating protein.

Embodiment 8

The cell-penetrating conjugate of any one of embodiments 1-7, wherein said biotin domain is attached to said phosphorothioate nucleic acid.

Embodiment 9

The cell-penetrating conjugate of embodiment 8, wherein said biotin domain is covalently attached to said phosphorothioate nucleic acid.

Embodiment 10

The cell-penetrating conjugate of embodiment 8 or 9, wherein a plurality of phosphorothioate nucleic acids are attached to said biotin domain.

Embodiment 11

The cell-penetrating conjugate of any one of embodiments 1-10, wherein said phosphorothioate nucleic acid is about 10, 20, 30, 40, 50, 60, 70, 80, 90, 100 or more nucleic acid residues in length.

Embodiment 12

The cell-penetrating conjugate of embodiment 11, wherein said phosphorothioate nucleic acid is from about 10 to about 30 nucleic acid residues in length.

Embodiment 13

The cell-penetrating conjugate of embodiment 11, wherein said phosphorothioate nucleic acid is about 20 nucleic acid residues in length.

Embodiment 14

The cell penetrating conjugate of any one of embodiments 1 to 12, wherein said non-cell penetrating protein has a molecular weight of more than 25 kD.

Embodiment 15

The cell penetrating conjugate of any one of embodiments 1 to 14, wherein said non-cell penetrating protein has a molecular weight of about 25 kD to about 750 kD.

Embodiment 16

The cell penetrating conjugate of any one of embodiments 1 to 15, wherein said non-cell penetrating protein is an antibody.

Embodiment 17

The cell penetrating conjugate of embodiment 16, wherein said antibody is an IgG antibody.

Embodiment 18

The cell penetrating conjugate of embodiment 16, wherein said antibody is an IgA, IgM, IgD or IgE antibody.

Embodiment 19

The cell penetrating conjugate of embodiment 16, wherein said antibody is an Fv fragment.

Embodiment 20

The cell penetrating conjugate of any one of embodiments 16 to 19, wherein the antibody is a humanized antibody.

Embodiment 21

The cell penetrating conjugate of any one of embodiments 1 to 20, wherein said non-cell penetrating protein binds an intracellular target.

Embodiment 22

The cell penetrating conjugate of embodiment 21, wherein said intracellular target is a target of a disease selected from the group consisting of autoimmune disease, inflammatory disease, metabolic disorder, developmental disorder, cardiovascular disease, liver disease, intestinal disease, infectious disease, endocrine disease, neurological disorder, and cancer.

Embodiment 23

The cell penetrating conjugate of embodiment 21 or 22, wherein said intracellular target is a signaling molecule or a transcription factor.

Embodiment 24

The cell penetrating conjugate of embodiment 23, wherein said signaling molecule is a phosphatase or a kinase.

Embodiment 25

The cell penetrating conjugate of embodiment 21, wherein said intracellular target is a cancer target.

Embodiment 26

The cell penetrating conjugate of embodiment 21, wherein said intracellular target is selected from the group consisting of STAT3, and Src.

Embodiment 27

The cell penetrating conjugate of embodiment 21, wherein said intracellular target is phosphorylated Src.

Embodiment 28

The cell penetrating conjugate of any one of embodiments 1 to 27, wherein said non-cell penetrating protein further comprises a label, a small molecule or a functional nucleic acid attached to said protein.

Embodiment 29

The cell penetrating conjugate of any one of embodiments 1 to 28, wherein said cell penetrating conjugate is bound to an intracellular target.

Embodiment 30

A method of forming a cell penetrating conjugate, said method comprising contacting a non-cell penetrating protein with a phosphorothioate nucleic acid, wherein said non-cell penetrating protein is attached to a first member of a biotin binding pair and said phosphorothioate nucleic acid is attached to a second member of said biotin binding pair, thereby forming a cell penetrating conjugate comprising a non-covalent bond between a biotin domain and biotin-binding domain.

Embodiment 31

The method of embodiment 30, wherein said first member of said biotin binding pair is a biotin-binding domain.

Embodiment 32

The method of embodiment 30, wherein said second member of said biotin binding pair is a biotin domain.

Embodiment 33

The method of embodiment 30, wherein said first member of said biotin binding pair is a biotin domain.

Embodiment 34

The method of embodiment 30, wherein said second member of said biotin binding pair is a biotin-binding domain.

Embodiment 35

The method of embodiment 30, wherein said phosphorothioate nucleic acid comprises a covalent reactive moiety.

Embodiment 36

A cell comprising the cell penetrating conjugate of any one of embodiments 1 to 29.

Embodiment 37

A pharmaceutical composition comprising the cell penetrating conjugate of any one of embodiments 1 to 29 and a pharmaceutically acceptable carrier.

Embodiment 38

The pharmaceutical composition of embodiment 37, further comprising a second non-cell penetrating protein comprising a second non-covalent linker attaching one or more phosphorothioate nucleic acids to said second non-cell penetrating protein.

Embodiment 39

The pharmaceutical composition of embodiment 38, wherein said non-covalent linker comprises a biotin-binding domain non-covalently attached to a biotin domain.

Embodiment 40

The pharmaceutical composition of embodiment 38, wherein said second non-cell penetrating protein binds an intracellular target.

Embodiment 41

The pharmaceutical composition of embodiment 40, wherein said second non-cell penetrating protein binds a different epitope on the intracellular target relative to said non-cell penetrating protein of any one of embodiments 21 to 27.

Embodiment 42

The pharmaceutical composition of embodiment 41, wherein said second non-cell penetrating protein binds a second intracellular target.

Embodiment 43

The pharmaceutical composition of any one of embodiments 38 to 42, wherein said second non-cell penetrating protein is an antibody.

Embodiment 44

A kit comprising the cell penetrating conjugate of any one of embodiments 1 to 29 or the pharmaceutical composition of embodiment 37 and instructions for use.

Embodiment 45

The kit of embodiment 44, further comprising a second non-cell penetrating protein comprising a second non-covalent linker attaching one or more phosphorothioate nucleic acids to said second non-cell penetrating protein.

Embodiment 46

The kit of embodiment 45, wherein said conjugate of any one of embodiments 1 to 29 and said second non-cell penetrating protein are in separate containers.

Embodiment 47

The kit of embodiment 45 or 46, wherein said second non-cell penetrating protein binds a different epitope on the intracellular target relative to the non-cell penetrating protein of any one of embodiments 1 to 29.

Embodiment 48

The kit of any one of embodiments 45 to 47, wherein said second non-cell penetrating protein binds a second intracellular target.

Embodiment 49

The kit of any one of embodiments 45 to 48, wherein said second non-cell penetrating protein is formulated as a pharmaceutical composition comprising the second non-cell penetrating protein and a pharmaceutically acceptable carrier.

Embodiment 50

The kit of any one of embodiments 45 to 49, wherein the second non-cell penetrating protein is an antibody.

Embodiment 51

A method of delivering a non-cell penetrating protein into a cell comprising contacting the cell with said cell penetrating conjugate of any one of embodiments 1 to 29.

Embodiment 52

The method of embodiment 51, wherein said non-cell penetrating protein binds the nuclear protein in the cytoplasm thereby forming a non-cell penetrating protein-nuclear protein complex.

Embodiment 53

The method of embodiment 52, wherein said non-cell penetrating protein-nuclear protein complex in not capable of entering the nucleus of the cell.

Embodiment 54

A method of treating a disease in a subject in need thereof, said method comprising administering to a subject an effective amount of the cell penetrating conjugate of any one of embodiments 1 to 29, thereby threating the disease in said subject.

Embodiment 55

The method of embodiment 54, further comprising administering to the subject a second non-cell penetrating protein comprising a second non-covalent linker attaching one or more phosphorothioate nucleic acids to said second non-cell penetrating protein.

Embodiment 56

The method of embodiment 55, wherein said non-covalent linker comprises a biotin-binding domain non-covalently attached to a biotin domain.

Embodiment 57

The method of embodiment 56, wherein said second non-cell penetrating protein binds a different epitope on the intracellular target relative to the conjugate of any one of embodiments 1 to 29.

Embodiment 58

The method of embodiment 57, wherein the second non-cell penetrating protein binds a second intracellular target.

Embodiment 59

The method of any one of embodiments 55 to 58, wherein the conjugate of any one of embodiments 1 to 29 and said second non-cell penetrating protein are administered simultaneously.

Embodiment 60

The method of any one of embodiments 55 to 58, wherein said conjugate of any one of embodiments 1 to 29 and said second non-cell penetrating protein are administered sequentially.

Embodiment 61

The method of any one of embodiments 55 to 60, wherein said second non-cell penetrating protein is an antibody.

Embodiment 62

The method of any one of embodiments 55 to 61, further comprising administering a second therapeutic agent to the subject.

Embodiment 63

The method of any one of embodiments 55 to 62, wherein said disease is selected from the group consisting of autoimmune disease, developmental disorder, inflammatory disease, metabolic disorder, cardiovascular disease, liver disease, intestinal disease, infectious disease, endocrine disease, neurological disorder, and cancer.

Embodiment 64

The method of embodiment 63, wherein the disease is cancer.

Embodiment 65

The method of embodiment 55, wherein the non-cell penetrating protein of the conjugate binds an intracellular target and the intracellular target is STAT3 or Src.

Embodiment 66

The method of embodiment 55, wherein the non-cell penetrating protein of the conjugate binds an intracellular target and the intracellular target is phosphorylated Src.

Embodiment 67

The method of embodiment 55, wherein the non-cell penetrating protein of the conjugate is an antibody that specifically binds STAT3 and the second non-cell penetrating protein is an antibody that specifically binds another epitope of STAT3.

What is claimed is:

1. A cell-penetrating conjugate comprising:
   (i) an antibody;
   (ii) a phosphorothioate nucleic acid; and
   (iii) a non-covalent linker attaching said phosphorothioate nucleic acid to said antibody, said non-covalent linker comprising a biotin-binding domain non-covalently attached to a biotin domain;
   wherein said phosphorothioate nucleic acid enhances intracellular delivery of said antibody;
   wherein said phosphorothioate nucleic acid is from about 5 to about 50 nucleic acid residues in length;
   wherein said antibody binds an intracellular target;
   wherein said intracellular target is STAT3 or Src; and
   wherein said antibody is non-cell penetrating in the absence of said phosphorothioate nucleic acid.

2. The cell-penetrating conjugate of claim 1, wherein said biotin-binding domain is a streptavidin domain.

3. The cell-penetrating conjugate of claim 1, wherein a plurality of biotin-binding domains are attached to said antibody.

4. The cell-penetrating conjugate of claim 1, wherein said biotin domain is attached to said phosphorothioate nucleic acid.

5. The cell-penetrating conjugate of claim 4, wherein a plurality of phosphorothioate nucleic acids are attached to said biotin domain.

6. The cell-penetrating conjugate of claim 1, wherein said phosphorothioate nucleic acid is about 20 nucleic acid residues in length.

7. The cell penetrating conjugate of claim 1, wherein said antibody has a molecular weight of more than 25 kDa.

8. A cell comprising the cell penetrating conjugate of claim 1.

9. A pharmaceutical composition comprising the cell penetrating conjugate of claim 1 and a pharmaceutically acceptable carrier.

10. The pharmaceutical composition of claim 9, further comprising a second antibody comprising a second non-covalent linker attaching one or more phosphorothioate nucleic acids to said second antibody.

11. The cell penetrating conjugate of claim 1, wherein the antibody binds phosphorylated Src.

12. The pharmaceutical composition of claim 10, wherein the antibody of the cell penetrating conjugate specifically binds STAT3 and the second antibody specifically binds another epitope of STAT3.

13. A method of delivering an antibody into a cell comprising contacting the cell with said cell penetrating conjugate of claim 1.

* * * * *